United States Patent [19]

Biftu et al.

[11] Patent Number: 5,114,961
[45] Date of Patent: May 19, 1992

[54] 2,5-DIARYL TETRAHYDOFURANS AND ANALOGS THEREOF AS PAF ANTAGONISTS

[75] Inventors: Tesfaye Biftu, Parlin; Robert L. Bugianesi, Colonia; Nirindar N. Girotra, Parlin; Mitree M. Ponpipom, Branchburg; Soumya P. Sahoo, Edison; Chan H. Kuo, South Plainfield, all of N.J.

[73] Assignee: Merck & Co., Inc., Rahway, N.J.

[21] Appl. No.: 624,449

[22] Filed: Dec. 10, 1990

Related U.S. Application Data

[62] Division of Ser. No. 362,915, Jun. 8, 1989, Pat. No. 4,996,203.

[51] Int. Cl.⁵ .................. C07D 407/12; A61K 31/415
[52] U.S. Cl. ..................................... 514/397; 548/336
[58] Field of Search ......................... 548/336; 514/397

[56] References Cited

U.S. PATENT DOCUMENTS

| | | | |
|---|---|---|---|
| 3,769,350 | 10/1973 | Perry et al. | 514/461 |
| 4,539,332 | 9/1985 | Biftu et al. | 514/461 |
| 4,595,693 | 5/1986 | Biftu et al. | 514/461 |
| 4,757,084 | 7/1988 | Biftu et al. | 514/438 |
| 4,977,146 | 12/1990 | Biftu | 514/99 |
| 4,996,203 | 2/1991 | Biftu | 514/231.5 |
| 5,001,123 | 3/1991 | Biftu | 514/235 |
| 5,010,100 | 4/1991 | Biftu | 514/461 |
| 5,011,847 | 4/1991 | Biftu | 514/336 |

FOREIGN PATENT DOCUMENTS

| | | |
|---|---|---|
| 0154887 | 2/1985 | European Pat. Off. |
| 0144804 | 6/1986 | European Pat. Off. |
| 0199324 | 10/1986 | European Pat. Off. |
| 0217204 | 4/1987 | European Pat. Off. |

OTHER PUBLICATIONS

Chem. Abstracts vol. 42, Abstract 5836e (1948).
Chem. Abstracts vol. 79, Abstract 136925u (1973).
Chem. Abstracts vol. 81, Abstract 135662k (1974).
Chem. Abstracts vol. 83, Abstract 8676g (1975).
Chem. Abstracts vol. 86, Abstract 16468v (1977).
Chem. Abstracts vol. 90, Abstract 54746z (1979).
Chem. Abstracts vol. 96, Abstract 1225588a (1982).
Biftu, T., Hazra, G. B. Stevenson, R., and Williams, J. R., Synthesis of lignans, 2,3-diaroylbutanes J. Chem. Soc. pp. 1147-1150 (1978).
Biftu, T., Hazra, G. B. Stevenson, R., Synthesis of (+)-Deoxyschizandrin, J. Chem. Soc. pp. 2276-2281 (1979).
Hwang, S. B., Lam, M. H., Biftu, T., Beattie, T. R., Asghen, T. Y., Trans-2,5-bis-(3,4,5-trimethoxyphenyl) tetrahydrofuran, J. Biol. Chem. vol. 260, No. 29, pp. 15639-15645 (Dec. 1985).
Sarkanen, K. V. and Wallis, A. F. A., Oxidative Dimerization's of (E)- and (Z)-Isoeugenol (2-Methoxy-4-propenylphenol) and (E)- and (Z)-2,6-dimethoxy-4-propenyl-phenol, J. Chem. Soc., Perkin transactions, pp. 1869-1878 (1973).
Stevenson, R., Williams, J. R., Synthesis of Tetrahydrofuran lignans, (+)-Galbelgin and (+)-Grandisin, Tetrahedron, vol. 33, pp. 285-288 (1977).

*Primary Examiner*—Robert Gerstl
*Attorney, Agent, or Firm*—Curtis C. Panzer

[57] ABSTRACT

The present invention is directed to a specifically substituted tetrahydrofuran of the formula (I)

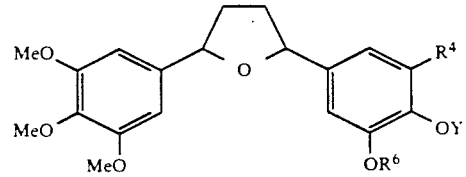

wherein $R^4$ is an alkylthio, alkylsulfinyl or alkylsulfonyl containing group and at least one of the substituents at positions 3, 4 or 5 contains a heterocyclic, heteroaryl or substituted phenylthio moiety.

16 Claims, No Drawings

2,5-DIARYL TETRAHYDOFURANS AND ANALOGS THEREOF AS PAF ANTAGONISTS

This is a division of application Ser. No. 362,915, filed Jun. 8, 1989, U.S. Pat. No. 4,996,203.

BACKGROUND OF THE INVENTION

Platelet-activating factor (PAF) has recently been identified as an acetyl glyceryl ether phosphoryl-choline (AGEPC), i.e., 1-O-hexadecyl/octadecyl-2-acetyl-sn-glyceryl-3-phosphorylcholine (Hanahan D. J., et al., *J. Biol. Chem.* 255:5514, 1980). Even before its chemical identification, PAF had been linked to various biological activities and pathways making it one of the important mediators responsible for a variety of physiological processes including activation or coagulation of platelets, pathogenesis of immune complex deposition, smooth muscle contraction, inflammation, hypotension, shock, pain, edema as well as respiratory, cardiovascular and intravascular alterations. Since these physiological processes are in turn associated with a large group of diseases, for example, inflammatory disease, cardiovascular disorder, hypotension, shock, psoriasis, allergic and skin diseases, asthma, lung edema, peptic or stomach ulcer, dental pain, and adult respiratory distress syndrome, more and more scientific investigation has been focused on the search of a PAF antagonist or inhibitor for treating or preventing these common diseases.

The compounds of the present invention are specific PAF antagonists. They are similar to a subclass of compounds called lignans which characteristically contain two phenylpropyl groups bonded at the β-carbon. Tetrahydrofuran (THF) derivatives can exist in eight different stereochemical configurations as shown in Scheme I.

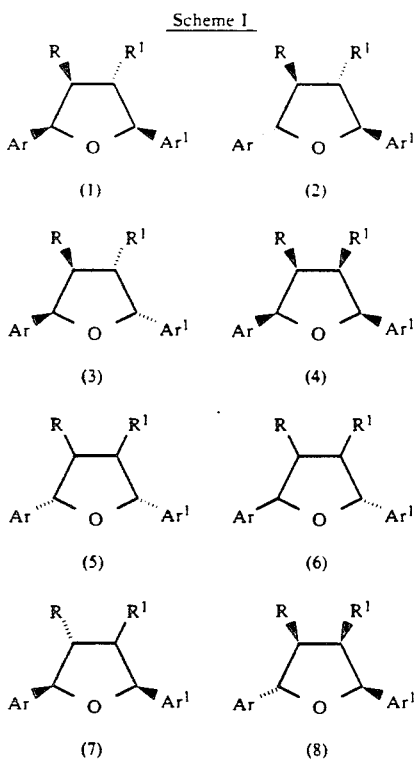

Scheme I

We have been able to prepare all the possible isomers of the tetrahydrofuran lignan analogs with different substituents and found that activity is stereospecific.

Accordingly, the present invention is directed to the preparation of the most potent isomers of known or novel tetrahydrofuran derivatives as PAF antagonists and use them for the treatment of various diseases including prevention of platelet aggregation, hypotension, inflammation, asthma, lung edema, adult respiratory distress syndrome, various shock syndromes, cardiovascular disorders and other related skeletal-muscular disorders, graft-host rejection, nephritis, pancreatitis, and lupus.

The present invention is also directed to acceptable pharmaceutical compositions containing one or more of the tetrahydrofuran derivatives and/or analogs as the active ingredient. As PAF antagonists, these novel compositions should be effective in the treatment of various skeletal-muscular related diseases.

The present invention is also directed to a method of treatment comprising the administration of a therapeutically sufficient amount of these PAF antagonists to a patient suffering from various skeletal-muscular disorders including inflammation, e.g., osteoarthritis, rheumatoid arthritis and gout, hypotension, shock, psoriasis, allergic or skin diseases, asthma, pain especially dental pain, peptic or stomach ulcer, lung edema, adult respiratory distress syndrome or cardiovascular disorders, graft-host rejection, nephritis, pancreatitis, and lupus.

BRIEF DESCRIPTION OF THE INVENTION

The present invention is directed to a specifically substituted tetrahydrofuran of the formula (I)

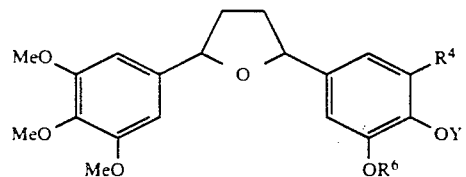

wherein $R^4$ is an alkylthio, alkylsulfinyl or alkylsulfonyl containing group and at least one of the substituents at positions 3,4 or 5 contains a heterocyclic, heteroaryl or substituted phenylthio moiety.

DETAILED DESCRIPTION OF THE INVENTION

The present invention is directed to compounds of the following structural formula:

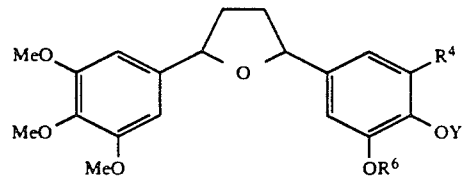

or pharmaceutically acceptable salts thereof wherein:
$R^4$ is
(a) $S(O)_nR^2$ in which n is 0,1 or 2 and $R^2$ is selected from the group consisting of
   (1) $C_{1-6}$alkyl, (2) substituted $C_{1-6}$alkyl wherein the substituent is selected from the group consisting of hydroxy, and amino,
(3) $C_{2-6}$alkenyl,
(4) $C_{1-6}$alkylcarbonyl-$C_{1-6}$alkyl,
(5) N-substituted $C_{1-6}$aminoalkyl, wherein the substituent is $C_{1-6}$alkyl,
(6) N,N-di-substituted $C_{1-6}$aminoalkyl, wherein the substituents each independently represent $C_{1-6}$alkyl,
(7) imidazolyl-$C_{1-6}$alkyl,
(8) pyrrolidinyl-$C_{1-6}$alkyl,
(9) morpholinyl-$C_{1-6}$alkyl,
(10) thiazolinyl-$C_{1-6}$alkyl,
(11) piperidinyl-$C_{1-6}$alkyl,
(b) imidazolylcarbonyl,
(c) morpholinylcarbonyl,
(d) morpholinyl-$C_{1-6}$alkylaminocarbonyl,
(e) N-pyrryl, and
(f) thiazolylcarbonyl;
Y is selected from the group consisting of
(a) $C_{1-12}$alkyl,
(b) substituted $C_{1-8}$alkyl wherein the substituent is selected from the group consisting of hydroxy, and amino,
(c) $C_{1-8}$alkoxy-$C_{1-6}$alkyl,
(d) $C_{2-6}$alkenyl,
(e) $C_{1-6}$alkyl $S(O)_m$—$C_{1-6}$alkyl in which m is 0, 1 or 2,
(f) pyridyl-$C_{1-6}$alkyl,
(g) pyridylthio-$C_{1-6}$alkyl,
(h) morpholinyl-$C_{1-6}$alkyl,
(i) hydroxyphenylthio-$C_{1-6}$alkyl,
(j) cyanophenylthio-$C_{1-6}$alkyl,
(k) imidazolylthio-$C_{1-6}$alkyl,
(l) triazolylthio-$C_{1-6}$alkyl,
(m) triazolylphenylthio-$C_{1-6}$alkyl,
(n) tetrazolylthio-$C_{1-6}$alkyl,
(o) tetrazolylphenylthio-$C_{1-6}$alkyl,
(p) aminophenylthio-$C_{1-6}$alkyl,
(q) N,N-di-substituted aminophenylthio-$C_{1-6}$-alkyl wherein the substituents each independently represent $C_{1-6}$alkyl,
(r) amidinophenylthio-$C_{1-6}$alkyl,
(s) phenylsulfinyl $C_{1-6}$alkyl, and
(t) phenylsulfonyl $C_{1-6}$alkyl;
$R^6$ is selected from the group consisting of
(a) $C_{1-6}$alkyl,
(b) substituted $C_{1-6}$alkyl wherein the substituent is selected from the group consisting of hydroxy and amino,
(c) $C_{1-6}$alkyl-O—$R^{10}$, wherein $R^{10}$ is
(1) —$PO_2(OH)^- M^+$ wherein $M^{30}$ is a pharmaceutically acceptable cation,
(2) —$C(O)(CH_2)_2$—$CO_2^- M^+$, or
(3) —$SO_3^- M^+$,
(d) $C_{1-6}$-alkylcarbonyl-$C_{1-6}$alkyl,
(e) $C_{1-6}$carboxyalkyl,
(f) $C_{1-4}$alkylamino-$C_{1-6}$alkyl,
(g) N,N-di-substituted $C_{1-6}$aminoalkyl wherein the substituents each independently represent $C_{1-6}$alkyl,
(h) pyridyl-$C_{1-6}$alkyl,
(i) imidazolyl-$C_{1-6}$alkyl,
(j) imidazolyl-X-$C_{1-6}$alkyl wherein X is thio or amino,
(k) morpholinyl-$C_{1-6}$alkyl,
(l) pyrrolidinyl-$C_{1-6}$alkyl,
(m) thiazolinyl-$C_{1-6}$alkyl,
(n) piperidinyl-$C_{1-6}$alkyl,
(o) morpholinyl-$C_{1-6}$hydroxyalkyl,
(p) N-pyrryl,
(q) piperazinyl-$C_{1-6}$alkyl,
(r) N-substituted piperazinyl-$C_{1-6}$alkyl, wherein the substituent is $C_{1-4}$alkyl,
(s) triazolyl-$C_{1-6}$alkyl,
(t) tetrazolyl-$C_{1-6}$alkyl,
(u) tetrazolylamino-$C_{1-6}$alkyl, and
(v) thiazolyl-$C_{1-6}$alkyl,
provided that at least one of $R^4$, Y and $R^6$ contains a heterocyclic, heteroaryl or a substituted phenylthio moiety.

As will be understood by those skilled in the art, pharmaceutically acceptable salts are intended to include but are not limited to salts with inorganic acids such as hydrochloride, sulfate, phosphate, diphosphate, hydrobromide and nitrate or salts with an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations are intented to include but are not limited to sodium, potassium, calcium, aluminum, lithium and ammonium.

One embodiment of the present invention are the compounds of formula (I) wherein the substituents as positions 2 and 5 of the tetrahydrofuran are in a trans relationship to one another, and
$R^6$ is a substituted heterocyclic group selected from the group consisting of
(a) pyridyl-$C_{1-6}$alkyl,
(b) imidazolyl-$C_{1-6}$alkyl,
(c) imidazolyl-X-$C_{1-6}$alkyl wherein X is thio or amino,
(e) morpholinyl-$C_{1-6}$alkyl,
(e) pyrrolidinyl-$C_{1-6}$alkyl,
(f) morpholinyl-$C_{1-6}$alkyl,
(g) thiazolinyl-$C_{1-6}$alkyl,
(h) piperidinyl-$C_{1-6}$alkyl,
(i) morpholinyl-$C_{1-6}$hydroxyalkyl,
(j) N-pyrryl,
(k) piperazinyl-$C_{1-6}$alkyl,
(l) N-substituted piperazinyl-$C_{1-6}$alkyl, wherein the substituent is $C_{1-4}$alkyl,
(m) triazolyl-$C_{1-6}$alkyl,
(n) tetrazolyl-$C_{1-6}$alkyl,
(o) tetrazolylamino-$C_{1-6}$alkyl, and
(p) thiazolyl-$C_{1-6}$alkyl.

Illustrating this embodiment is the class of compounds of the formula (I) wherein
$R^4$ is $S(O)_n R^2$, n is 2 and $R^2$ is selected from the group consisting of
(a) $C_{1-6}$alkyl,
(b) substituted $C_{1-6}$alkyl wherein the substituent is selected from hydroxy, oxo and amino,
(c) N-substituted $C_{1-6}$aminoalkyl, wherein the substituent is $C_{1-6}$alkyl, and
(d) N,N-di-substituted $C_{1-6}$aminoalkyl, wherein the substituents each independently represent $C_{1-6}$alkyl.

A subclass of these compounds is the compounds of formula (I) wherein Y is $C_{1-12}$ alkyl or hydroxy $C_{1-8}$ alkyl.

A smaller subclass of these compounds is the compounds of formula (I) wherein $R^6$ is selected from the group consisting of
(a) pyridyl-$C_{1-6}$alkyl,
(b) imidazolyl-$C_{1-6}$alkyl, (c) imidazolyl-X-$C_{1-6}$alkyl wherein X is thio or amino,
(d) morpholinyl-$C_{1-6}$alkyl,
(e) morpholinyl-$C_{1-6}$hydroxyalkyl,
(f) piperazinyl-$C_{1-6}$alkyl,
(g) triazolyl-$C_{1-6}$alkyl,
(h) pyrrolidinyl-$C_{1-6}$alkyl, and
(i) piperidinyl-$C_{1-6}$alkyl.

A still smaller subclass of these compounds is the compounds of formula (I) wherein $R^2$ is selected from the group consisting of
(a) $C_{1-3}$alkyl,
(b) $C_{1-3}$alkylcarbonyl-$C_{1-3}$alkyl,
(c) hydroxy $C_{1-4}$alkyl; and
Y is n-propyl.

Exemplifying this subclass are those compounds of the formula (I) which are:
(a) trans-2-[3-(2-Oxopropylsulfonyl)-4-n-propoxy-5-{3-(1-morpholino)-n-propoxy}phenyl]-5-(3,4,5-trimethoxyphenyl)tetrahydrofuran,
(b) trans-2-[3-(2-hydroxypropyl-sulfonyl)-4-propoxy-5-{3-(1-morpholino)-n-propoxy}phenyl]-5-(3,4,5-trimethoxyphenyl)tetrahydrofuran.
(c) trans-2-[3-(2-Oxopropylsulfonyl)-4-n-propoxy-5-{2-(1-morpholino)-n-ethoxy}phenyl]-5-(3,4,5-trimethoxyphenyl)tetrahydrofuran,
(d) trans-2-[3-(2-Oxopropylsulfonyl)-4-n-propoxy-5-{4-(1-morpholino)-n-butoxy}phenyl]-5-(3,4,5-trimethoxyphenyl)tetrahydrofuran,
(e) trans-2-[3-(2-Oxopropylsulfonyl)-4-n-propoxy-5-{3-(1-piperizinyl)-n-propoxy}phenyl]-5-(3,4,5-trimethoxyphenyl)tetrahydrofuran,
(f) trans-2-[3-(2-Oxopropylsulfonyl)-4-n-propoxy-5-{2-(1-pyrrolidino)-n-ethoxy}phenyl]-5-(3,4,5-trimethoxyphenyl)tetrahydrofuran,
(g) trans-2-[3-(2-Oxopropylsulfonyl)-4-n-propoxy-5-[3-(1-pyrrolidino)-n-propoxy}phenyl]-5-(3,4,5-trimethoxyphenyl)tetrahydrofuran.
(h) trans-2-[3-(2-Oxopropylsulfonyl)-4-n-propoxy-5-{2-(1-piperidinyl)-n-ethoxy}phenyl]-5-(3,4,5-trimethoxyphenyl)tetrahydrofuran.
(i) trans-2-[3-(2-Hydroxypropylsulfonyl)-4-n-propoxy-5-{2-(1-morpholino)-n-ethoxy}phenyl]-5-(3,4,5-trimethoxyphenyl)tetrahydrofuran,
(j) trans-2-[3-(2-Hydroxypropylsulfonyl)-4-n-propoxy-5-{3-(1-piperidinyl)-n-propoxy}phenyl]-5-(3,4,5-trimethoxyphenyl)tetrahydrofuran,
(k) trans-2-[3-(2-Oxopropylsulfonyl)-4-propoxy-5-{3-(1-imidazolyl)propoxy}phenyl]-5-(3,4,5)-trimethoxyphenyl) tetrahydrofuran,
(l) trans-2-[3-(2-Oxopropylsulfonyl)-4-propoxy-5-{3-(3-pyridyl)propoxy}phenyl]-5-(3,4,5-trimethoxyphenyl)tetrahydrofuran,
(m) trans-2-[3-(2-Oxopropylsulfonyl)-4-propoxy-5-{3-(1H-1,2,4-triazolyl-3-thio)propoxy-}phenyl]-5-(3,4,5-trimethoxyphenyl)tetrahydrofuran,
(n) trans-2-[3-(2-Hydroxypropylsulfonyl)-4-n-propoxy-5-{3-(1H-1,2,4-triazolyl-3-thio)propoxy}phenyl]-5-(3,4,5-trimethoxyphenyl)tetrahydrofuran,
(o) trans-2-[3-(2-Hydroxypropylsulfonyl)-4-n-propoxy-5-{2-(1-imidazolyl)ethoxy}phenyl]-5-(3,4,5-trimethoxyphenyl) tetrahydrofuran,
(p) trans-2-[3-(2-Hydroxypropylsulfonyl)-4-n-propoxy-5-{3-(1-imidazolyl)propoxy}phenyl]-5-(3,4,5-trimethoxyphenyl)tetrahydrofuran,
(q) trans-2-[3-(2-Hydroxypropylsulfonyl)-4-n-propoxy-5-{4-(1-imidazolyl)butoxy}phenyl]-5-(3,4,5-trimethoxyphenyl) tetrahydrofuran,
(r) trans-2-[3-(2-Hydroxypropylsulfonyl)-4-n-propoxy-5-{2-(2-imidazolylthio) ethoxy}phenyl]-5-(3,4,5-trimethoxyphenyl)tetrahydrofuran.
(s) trans-2-[3-(2-Hydroxypropylsulfonyl)-4-n-propoxy-5-{3-(2-imidazolylthio) propoxy}phenyl]-5-(3,4,5-trimethoxyphenyl)tetrahydrofuran,
(t) trans-2-[3-(2-Oxopropylsulfonyl)-4-n-propoxy-5-{2-(2-imidazolylthio) ethoxy}phenyl]-5-(3,4,5-trimethoxyphenyl)tetrahydrofuran,
(u) trans-2-[3-(2-Oxopropylsulfonyl)-4-n-propoxy-5-{3-(2-imidazolylthio) propoxy}phenyl]-5-(3,4,5-trimethoxyphenyl)tetrahydrofuran,
(v) trans-2-[3-(2-Oxopropylsulfonyl)-4-n-propoxy-5-{4-(2-imidazolylthio) butoxy}phenyl]-5-(3,4,5-trimethoxyphenyl)tetrahydrofuran,
(w) trans-2-[3-n-Propylsulfonyl-4-(6-hydroxy-n-hexyloxy)-5-{2-(1-morpholino)-ethoxy}phenyl]5-(3,4,5-trimethoxyphenyl)tetrahydrofuran,
(x) trans-2-[3-n-Propylsulfonyl-4-(6-hydroxyhexyloxy)-5-{3-(1-morpholino)propoxy}phenyl]-5-trimethoxyphenyl)tetrahydrofuran,
(y) trans-2-[3-(3-Hydroxybutyl)sulfonyl-4-n-propoxy-5-(3-{1-morpholino}-n-propoxy)phenyl]-5-(3,4,5-trimethoxyphenyl)tetrahydrofuran,
(z) trans-2-[3-(2-hydroxypropyl)sulfonyl-4-n-propoxy-5-(2-imidazolyl)methoxyphenyl]-5 -(3,4,5-trimethoxyphenyl)tetrahydrofuran,
and their stereochemical isomers in the (2S,5S) configuration, Particularly exemplifying the first embodiment of the invention are
(a) trans-2-[3-(2-Oxopropylsulfonyl)-4-n-propoxy-5-{3-(1-morpholino)-n-propoxy}phenyl]-5-(3,4,5-trimethoxyphenyl) tetrahydrofuran,
(b) trans-2-[3-(2-Oxopropylsulfonyl)-4-propoxy-5-{3-(1-imidazolyl)propoxy}phenyl]-5-(3,4,5-trimethoxyphenyl) tetrahydrofuran,
(c) trans-2-[3-(2-Hydroxypropylsulfonyl)-4-n-propoxy-5-{3-(1-morpholino)-n-propoxy}phenyl]-5-(3,4,5-trimethoxyphenyl)tetrahydrofuran,
and their (2S,5S) stereoisomers which are
(d) (−)-(2S,5S)-2-[3-(2-Oxopropylsulfonyl)-4-n-propoxy-5-{3-(1-morpholino-n-propoxy}phenyl]-5-(3,4,5-trimethoxyphenyl)tetrahydrofuran,
(e) (−)-(2S,5S)-2-[3-(2-Oxopropylsulfonyl)-4-propoxy-5-{3-(1 -imidazolyl)propoxy}phenyl]-5-(3,4,5)-trimethoxyphenyl) tetrahydrofuran.
(f) (2S,5S)-2-[3-(2-Hydroxypropylsulfonyl)-4-n-propoxy-5-{3-(1 -morpholino)-n-propoxy}phenyl]-5-(3,4,5-trimethoxyphenyl)tetrahydrofuran.

A second embodiment of the present invention are the compounds of formula (I) wherein the substituents at positions 2 and 5 of the tetrahydrofuran are in a trans relationship to one another, and
$R^4$ is a substituted heterocyclic group selected from the group consisting of
(a) $S(O)_nR^2$, in which n is 2, and $R^2$ is
  (1) imidazolyl-$C_{1-6}$alkyl.
  (2) pyrrolidinyl-$C_{1-6}$alkyl,
  (3) morpholinyl-$C_{1-6}$alkyl,
  (4) thiazolinyl-$C_{1-6}$alkyl,
  (5) piperidinyl-$C_{1-6}$alkyl, or
(b) imidazolylcarbonyl,
(c) morpholinylcarbonyl,
(d) morpholinyl-$C_{1-6}$alkylaminocarbonyl
(e) N-pyrryl, and
(f) thiazolylcarbonyl.

Illustrating this embodiment is the class of compounds of the formula (I) wherein $R^6$ is
$R^6$ is selected from the group consisting of
(a) $C_{1-6}$alkyl,
(b) substituted $C_{1-6}$alkyl wherein the substituent is selected from the group consisting of hydroxy and amino,
(c) $C_{1-6}$alkylcarbonyl-$C_{1-6}$alkyl,
(d) $C_{1-6}$carboxyalkyl, and
(e) $C_{1-4}$-dialkylamino-$C_{1-6}$alkyl.

A subclass of these compounds is the compounds of formula (I) wherein R4 is $S(O)_nR^2$, in which n is 2, and $R^2$ is
(a) pyrrolidinyl-$C_{1-6}$alkyl, or
(b) morpholinyl-$C_{1-6}$alkyl; and
Y is $C_{1-6}$alkyl.

A smaller subclass of these compounds is the compounds of formula (I) wherein $R^6$ is selected from the group consisting of
(a) $C_{1-3}$alkyl,
(b) hydroxy $C_{1-4}$alkyl; and Y is ethyl or n-propyl.

Exemplifying this subclass are those compounds of the formula (I) which are
(a) trans-2-[3-(2-N-Pyrrolidinylethylsulfonyl)-4,5-dipropoxyphenyl]-5-(3,4,5-trimethoxyphenyl) tetrahydrofuran,
(b) trans-2-[3-(1-morpholinoethylsulfonyl)-4,5-dipropoxyphenyl]-5-(3,4,5-trimethoxyphenyl)tetrahydrofuran,
and their stereochemical isomers in the (2S,5S) configuration.

A third embodiment of the present invention are the compounds of formula (I) wherein the substituents at positions 2 and 5 of the tetrahydrofuran are in a trans relationship to one another, and
Y is a substituted heterocyclic group selected from the group consisting of
(a) pyridyl-$C_{1-6}$alkyl,
(b) pyridylthio-$C_{1-6}$alkyl,
(c) morpholinyl-$C_{1-6}$alkyl,
(d) hydroxyphenylthio-$C_{1-6}$alkyl,
(e) cyanophenylthio-$C_{1-6}$alkyl,
(f) imidazolylthio-$C_{1-6}$alkyl,
(g) triazolylthio-$C_{1-6}$alkyl,
(h) triazolylphenylthio-$C_{1-6}$alkyl,
(i) tetrazolylthio-$C_{1-6}$alkyl,
(j) tetrazolylphenylthio-$C_{1-6}$alkyl,
(k) aminophenylthio-$C_{1-6}$alkyl,
(l) $C_{1-6}$dialkylaminophenylthio-$C_{1-6}$alkyl,
(m) amidinophenylthio-$C_{1-6}$alkyl,
(n) phenylsulfinyl $C_{1-6}$alkyl, and
(o) phenylsulfonyl $C_{1-6}$alkyl.

Illustrating this embodiment is the class of compounds of the formula (I) wherein
$R^4$ is $S(O)_nR^2$, n is 2 and $R^2$ is selected from the group consisting of
(a) $C_{1-6}$alkyl,
(b) substituted $C_{1-6}$alkyl wherein the substituent is hydroxy or amino,
(c) $C_{2-6}$alkenyl,
(d) $C_{1-6}$alkylcarbonyl-$C_{1-6}$alkyl, and
(e) $C_{1-6}$diaminoalkyl.

A subclass of these compounds is the compounds of formula (I) wherein R6 is selected from the group consisting of
(a) $C_{1-6}$alkyl,
(b) substituted $C_{1-6}$alkyl wherein the substituent is hydroxy or amino.
(c) $C_{1-6}$alkylcarbonyl-$C_{1-6}$alkyl,
(d) $C_{1-6}$carboxyalkyl, and
(e) N,N-disubstituted-$C_{1-6}$alkyl wherein the substituents each independently represent $C_{1-6}$alkyl.

A smaller subclass of these compounds is the compounds of Formula (I) wherein Y is selected from the group consisting of
(a) pyridylthio-$C_{1-6}$alkyl,
(b) hydroxyphenylthio-$C_{1-6}$alkyl,
(c) cyanophenylthio-$C_{1-6}$alkyl,
(d) imidazolylthio-$C_{1-6}$alkyl,
(e) triazolylthio-$C_{1-6}$alkyl,
(f) tetrazolylphenylthio-$C_{1-6}$alkyl,
(g) N,N-disubstituted aminophenylthio-$C_{1-6}$alkyl, wherein the substituents each independently represent $C_{1-6}$alkyl,
(h) amidinophenylthio-$C_{1-6}$alkyl, and
(i) phenylsulfonyl $C_{1-6}$alkyl.

A still smaller subclass of these compounds is the compounds of formula (I) wherein $R^2$ is selected from the group consisting of
(a) $C_{1-6}$alkyl,
(b) substituted $C_{1-6}$alkyl wherein the substituent is hydroxy, and
(c) $C_{1-6}$alkylcarbonyl-$C_{1-6}$alkyl; and
$R_6$ is selected from the group consisting of
(a) $C_{1-6}$alkyl,
(b) substituted $C_{1-6}$alkyl wherein the substituent is hydroxy, and
(c) $C_{1-6}$alkylcarbonyl-$C_{1-6}$alkyl.

Exemplifying this subclass are those compounds of the formula (I) which are
(a) trans-2-[3-n-Propylsulfonyl-4-{2-(4-dimethyl-aminophenylthio)ethoxy}-5-methoxyphenyl]-5 -(3,4,5-trimethoxyphenyl) tetrahydrofuran,
(b) trans-2-[3-n-Propylsulfonyl-4-{2-(4-hydroxyphenylthio)ethoxy}-5-methoxy-phenyl]-5 -(3,4,5-trimethoxyphenyl) tetrahydrofuran,
(c) trans-2-[3-n-Propylsulfonyl-4-{2-(4-pyridylthio)ethoxy}-5-methoxyphenyl]-5 (3,4,5-trimethoxyphenyl) tetrahydrofuran,
(d) trans-2-[3-n-Propylsulfonyl-4-{2-(4-cyanophenylthio)ethoxy}-5-methoxyphenyl]-5 -(3,4,5-trimethoxyphenyl) tetrahydrofuran,
(e) trans-2-[3-n-Propylsulfonyl-4-{2-(4-amidinophenylthio)ethoxy}-5-methoxyphenyl]-5-( 3,4,5-trimethoxyphenyl) tetrahydrofuran,
(f) trans-2-[3-n-Propylsulfonyl-4-{2-(4-(2-tetrazo)-phenylthio)ethoxy}-5-methoxyphenyl]-5-(3,4,5-trimethoxyphenyl) tetrahydrofuran,
(g) trans-2-[3-n-Propylsulfonyl-4-{2-(2-imidazolthio)ethoxy}-5-methoxyphenyl]-5-(3,4,5-trimethoxyphenyl) tetrahydrofuran,
(h) trans-2-[3-n-Propylsulfonyl-4{2-(3-triazolthio)ethoxy}-5-methoxyphenyl]-5-(3,4,5-trimethoxyphenyl)tetrahydrofuran, and their stereochemical isomers in the (2S, 5S) configuration.

The compounds of formula (I) may be prepared by the methods shown in the following reaction schemes wherein $R^2$, Y, and $R^6$ are defined above, unless otherwise indicated. Also, as will be evident to those skilled in the art and as demonstrated in the Examples, reactive groups such as amino, hydroxy, carboxy, etc. may be protected by standard methods and subsequently deprotected when it is appropriate.

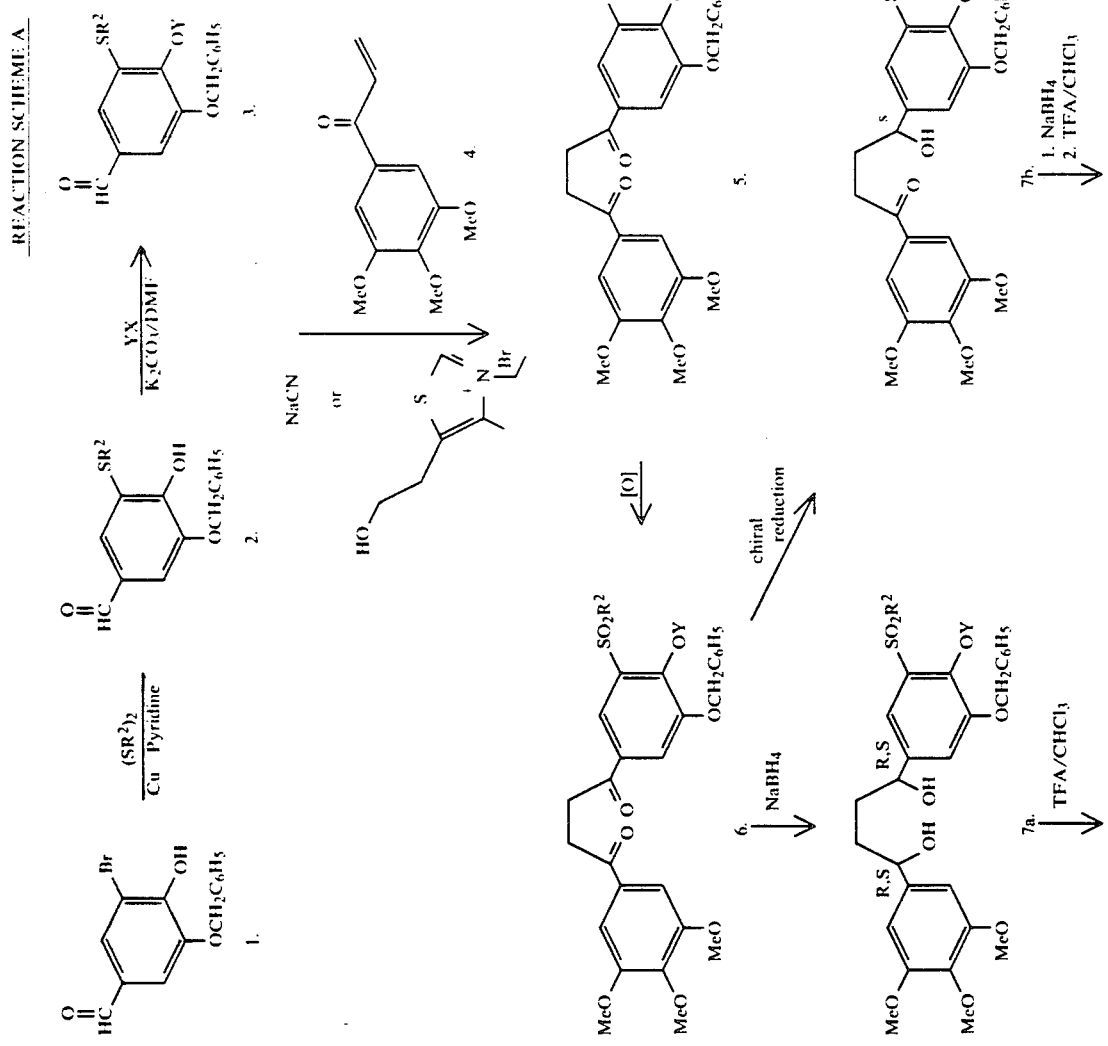

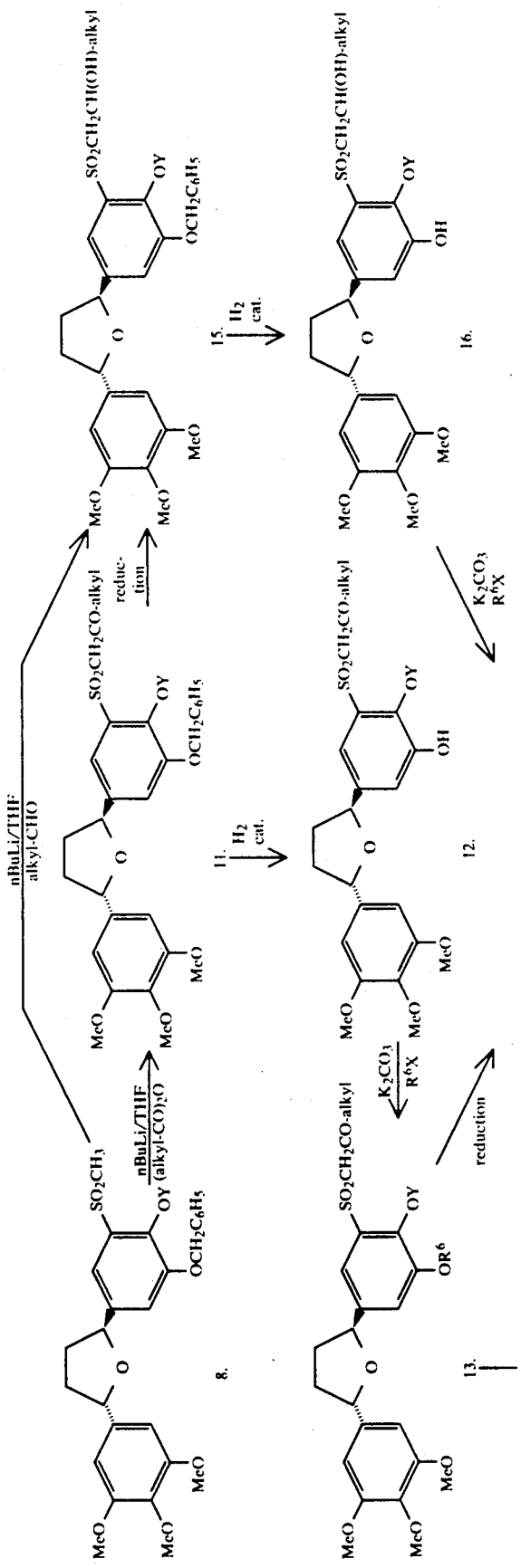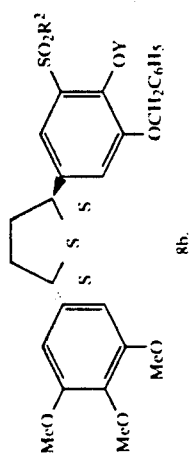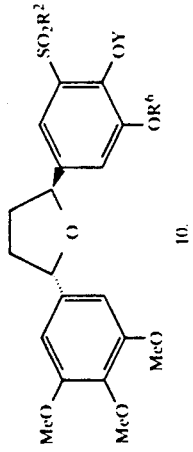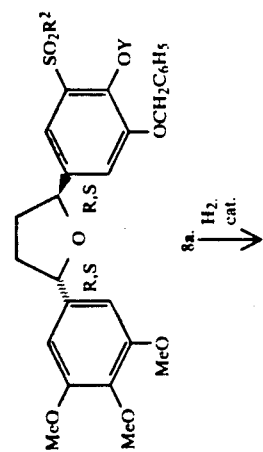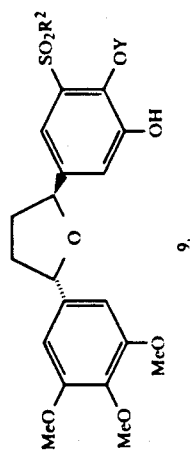

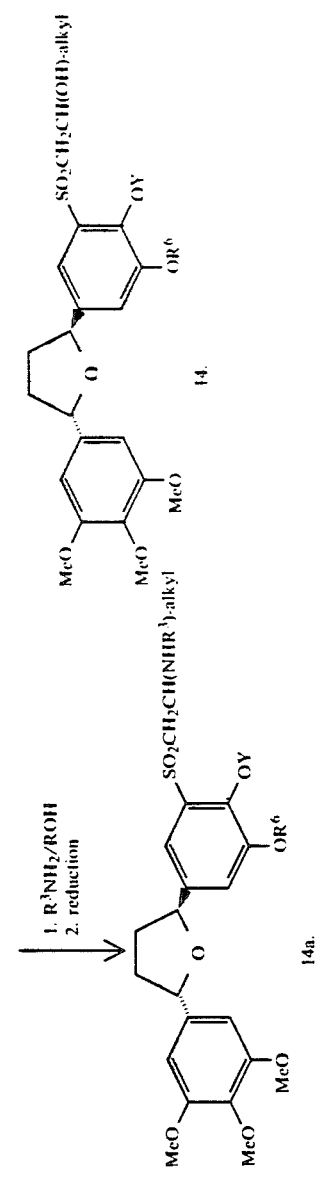

REACTION SCHEME B
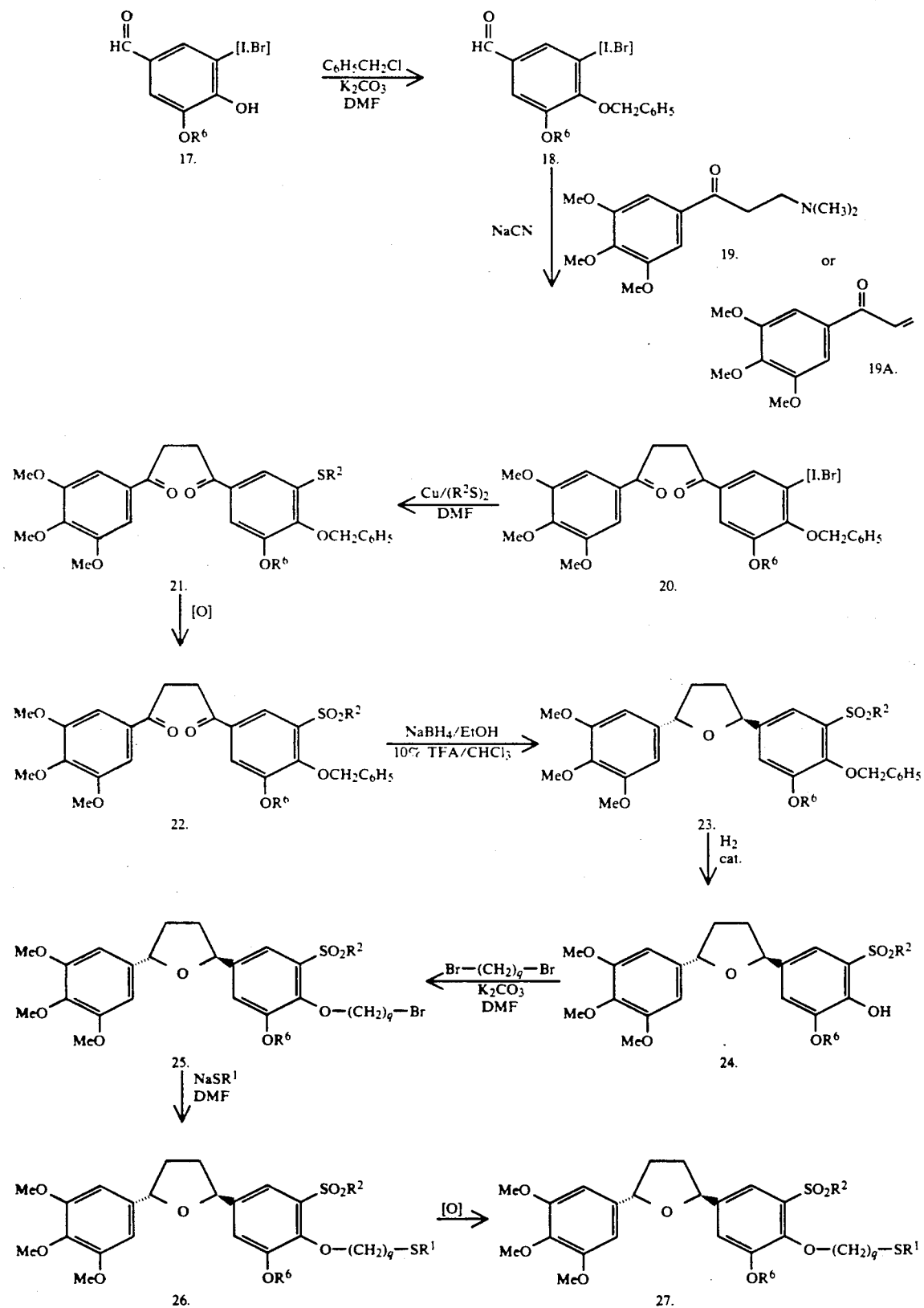

REACTION SCHEME C

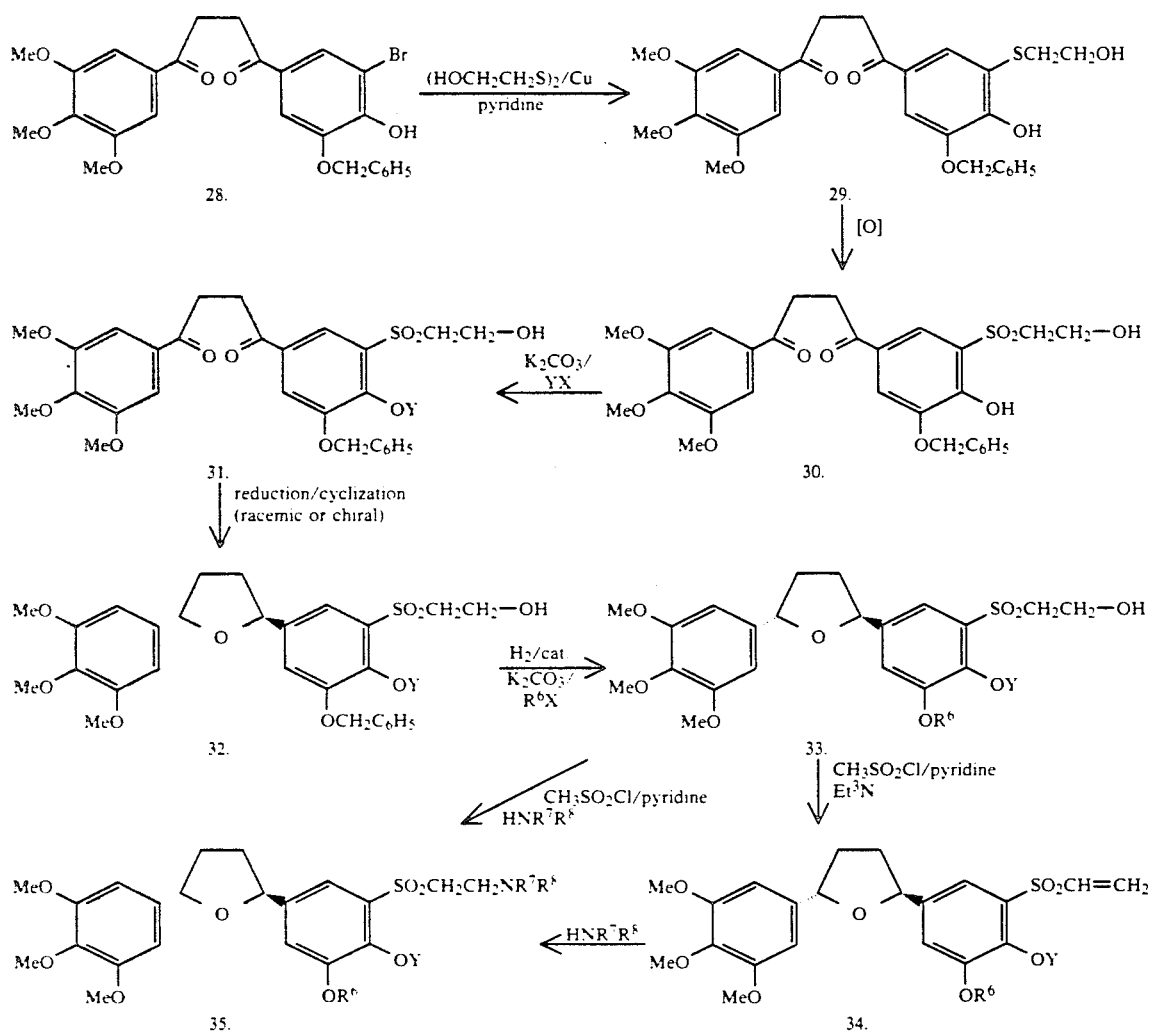

SCHEME A

The compounds of formula I may be prepared according to a sequence beginning with 5-benzyloxy-3-bromo-4-hydroxybenzaldehyde 1 which can be prepared according to the procedures outlined by J. Thiem [J. Chem. Soc Perkin I, 1186-1190 (1977)]. This compound is reacted with the appropriate disulfide $(SR^2)_2$, and copper powder in pyridine at elevated temperatures to provide compound 2. The 4-position may then be derivatized by alkylation with the appropriate alkylhalide, mesylate, or tosylate Y-X, using a base such as $K_2CO_3$ in a suitable solvent such as N,N-dimethylformamide (DMF) or tetrahydrofuran (THF) to provide compound 3. Alternatively, it is possible to prepare compound 3 by reversing the order of the last two steps. One of several alternative approaches to preparing diketone 5 is by reacting aldehyde 3 with vinylketone 4 and a base such as triethylamine with a catalytic amount of cyanide ion in DMF or 3-ethyl-5-(2-hydroxyethyl)-4-methylthiazolium bromide in DMF. Vinylketone 4 may be prepared from 3,4,5-trimethoxyacetophenone via conversion to a Mannich base, quaternization and elimination by standard procedures. Oxidation of the sulfide group of compound 5 with an oxidizing agent such as m-chloroperoxybenzoic acid (mCPBA) in methylene chloride ($CH_2Cl_2$) provides sulfone 6.

Furan 8a is prepared via reduction of diketone 6 with reducing agents such as sodium borohydride ($NaBH_4$) in a mixture of THF and methanol ($CH_3OH$) at 0° C. or lithium aluminum hydride ($LiAlH_4$) in diethylether or THF. Alternative methods include catalytic reduction using hydrogen and catalysts such as palladium, platinum, or rhodium. The resulting diol 7a is dissolved in chloroform ($CHCl_3$) and carefully reacted with a dilute solution of trifluoroacetic acid (TFA) in $CHCl_3$ at 0° C. If adequate care is taken with this reaction the trans-furan 8a is produced as the major product and can be separated from the cis diastereomer by chromatography on silica gel normally eluting with a mixture of hexanes and ethyl acetate. Alternative methods of furan formation from 7a include such reagents as methanesulfonyl chloride- triethylamine or triphenylphosphine dibromide The desired trans isomer 8a is usually a less polar material than the cis isomer on silica gel. The usually preferred chiral (−)-(S,S)-enantiomer may be prepared from diketone 6 by the specific reduction to hydroxyketone 7b using a bulky reducing agent such as lithium tri-t-butoxyaluminumhydride [$LiAlH(OtBu)_3$], or controlled reduction with $NaBH_4$. hydroxyketone 7b can be chemically resolved via the its mandelate esters to provide chiral (S)-hydroxyketone 7b.

Alternatively, compound 7b can be prepared in the chiral (S) form by using chiral reducing agent such as the lithium aluminumhydride-(S)-(−)-1,1'-bi-2-naphthol complex in THF normally at −78° C. Chiral transfuran 8b is prepared by sequential reduction of the remaining carbonyl group with NaBH$_4$ and cyclization with TFA as for compound 8a. the 5'-position is then derivatized by removal of the benzyl protecting group by standard deprotection methods such as hydrogenation using a catalyst such as palladium on carbon in a solvent such as ethanol (EtOH) or ethyl acetate. The free phenol may then be alkylated with the appropriate alkylating agent R$^6$X where X is a halide, mesylate or tosylate and a base such as K$_2$CO$_3$ in DMF, EtOH or another suitable solvent.

A variant of Scheme A is the further elaboration of compound 8a or 8b where R$^2$ is methyl. This compound may be acylated with by reaction with n-butyllithium in THF at −78° C. followed by an ester, acid chloride or anhydride such as ethyl acetate acetylchloride or acetic anhydride to give ketosulfone 11 which can be further elaborated into compound 13 by procedures previously outlined. A further elaboration is to reduce ketosulfone 13 to hydroxysulfone 14 using a reducing agent such as NaBH$_4$ in EtOH or THF and CH$_3$OH. Alternatively, compound 11 can be similarly reduced to hydroxysulfone 15 which can then be deprotected and alkylated to give 14. Alternatively, hydroxysulfone 15 can be produced directly from compound 8 by reaction with the appropriate aldehyde after reacting 8a or 8b with nButhyllithium or a similar base.

Other elaborations at position 3' may be carried out starting with compound 8a or 8b (R$^2$=CH$_3$, Ethyl, etc.) by procedures analogous to those describe herein.

A further series of amino compounds 14a can be prepared from ketosulfone 13 or 15 by reacting them hydroxylamine or substituted amines R$^3$NH$_2$ (wherein R$^3$ is $C_{1-6}$alkyl) is an alcoholic solvent such as ethanol (ETOH) to obtain oximes or imines. These imines or oximes may then be reduced to free or substituted amines 14a employing reducing agents such as sodium borohydride, sodium cyanoborohydride in ETOH or by catalytic hydrogenation by method s previously described.

SCHEME B

Scheme B is an alternative route to compounds of formula (I) which may be preferred for some compounds, in particular, those with elaborate Y-substituents such as Y=(CH$_2$)$_q$—SR$^1$, etc. (wherein R$^1$ is C$_{1-6}$alkyl heterocyclic heteroaryl or a substituted phenylthio as defined for Y in the detailed description)

Scheme B is similar to process A accept that one begins with compound 17 where R$^6$ is already attached such as 5-iodovanillin (R$^6$=CH$_3$) or other compounds. The 4-position of compound 17 is protected as the benzyl ether by standard procedures to give compound 18 which can be elaborated into racemic trans or chiral trans furans 23 by methods outlined for Process A. Furan 23 may be deprotected and elaborated as outlined for R$^6$ in Process A. An example shown here involves the alkylation of phenol 24 with a dibromoalkane such as dibromoethane in DMF with K$_2$CO$_3$ to give 25 (Y=—(CH$_2$)$_2$—Br).

Compound 25 may be further reacted with nucleophiles such as the sodium or potassium salts of substituted or unsubstituted arylthiols such as thiophenol. The sodium salts can be prepared by reacting the thiol compound in THF or DMF with sodium hydride (NaH). To this reaction mixture at room temperature is then added bromide 15 to give product 26. Sulfide 26 can be further elaborated to sulfone 27 by oxidation with mCPBA in CHCl$_3$.

SCHEME C: 3'-(2-aminoethyl)sulfone analogs (34)

A series of substituted or unsubstituted 2-aminoethylsulfone analogs 35 may be prepared by the scheme outlined in Scheme C. 2-hydroxyethylsulfone compounds 33 can be prepared by methods previously described and can then be derivatized as their tosylates or methanesulfonates by methods known to those in the art. Alternatively, the hydroxy group may be converted to a halide such as bromo, by one of a variety of commonly used methods such as triphenylphosphine and N-bromosuccinimide, or carbon tetrabromide or by phosphorous tribromide. elimination to vinylsulfone 34 may be achieved by reacting the bromide, tosylate, or mesylate with a tertiary amine such as triethylamine. The vinyl sulfone 34 may then be reacted with an amine R$^7$R$^8$NH (wherein R$^7$ and R$^8$ are each independently C$_{1-6}$alkyl) in a solvent such as acetonitrile producing aminoethylsulfones 35. Compounds of structure 35 may also be prepared from the precurser mesylates, etc. by reacting them directly with amines R$^7$R$^8$NH.

This invention also relates to a method of treatment for patients (or mammalian animals raised in the dairy, meat, or fur industries or as pets) suffering from disorders or diseases which can be attributed to PAF as previously described, and more specifically, a method of treatment involving the administration of the PAF antagonists of formula (I) as the active constituents.

Accordingly, the compounds of formula (I) can be used among other things to reduce pain and inflammation, to correct respiratory, cardiovascular, and intravascular alternations or disorders, and to regulate the activation or coagulation of platelets, to correct hypotension during shock, the pathogenesis of immune complex deposition and smooth muscle contractions.

For the treatment of inflammation such as rhumatoid arthritis, osteoarthritis, and eye inflammation, cardiovascular disorder, asthma, shock syndrome or other diseases mediated by the PAF, the compounds of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example a time delay material such as glyceryl monostearate or glyceryl distearate may be employed. They may also be coated by the techniques described in the U.S. Pat. Nos. 4,256,208; 4,166,452; and 4,265,874 to form osmotic therapeutic tablets for control release.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, emthylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of a an aqueous suspension by the addition of water provide the active ingredient in admixture with a dispersing or wetting agent, suspending agent and one or more preservative. Suitable dispersing or wetting agents and suspending agents are exemplified by those already mentioned above. Additional excipients, for example sweetening, flavoring nd coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gun acacia or gun tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such material are cocoa butter and polyethylene glycols.

For topical use, creams, ointments, jellies, solutions or suspensions, etc., containing the compounds of Formula (I) are employed.

Dosage levels of the order of from about 0.05 mg to about 140 mg per kilogram of body weight per day are useful in the treatment of the above-indicated conditions (about 2.5 mg to about 7 gms. per patient per day). For example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

A representative number of compounds of the instant invention of the formula (I) exhibit in vitro antagonistic activities with respect to PAF:

The compounds of formula (I) inhibit PAF-induced functions in both the cellular and tissue levels by changing the PAF in binding to its specific receptor site. The ability of a compound of formula (I) to inhibit the PAF binding to its specific receptor binding site on rabbit or human platelet or PMN plasma membranes was measured by a recently developed assay.

The inhibition of $^3[H]$-PAF or $^3[H]$-N-methyl carbamoyl-TAF binding to the human or rabbit platelet or PMN plasma membrane by a PAF antagonist of formula (I) was determined by a method employing isotopic labeling and filtration techniques. Generally, a series of Tris-buffered solutions of the selected antagonist at predetermined concentrations were prepared. Each of these solutions contains 1 pmole of $^3$H-PAF, a known amount of the test antagonist, and a sufficient amount of the pH 7.5 Tris-buffer solution (10mM Tris, 0.25% bovine serum albumin, and 150 mM NaCl per ml water) to make the final volume of 1 ml. After adding into a set of test tubes each with 100 μg of the platelet plasma membrane suspension (S. B. Hwang, et. al., *Biochemistry*, Vol. 22 pp. 4756–4763, 1983) and one of the Tris-buffer solutions described above, the resulting mixture in each test tube was incubated at 0° C. for about one hours or until the reaction was complete. Two control samples, one of which ($C_1$) contains all the ingredients described above except the antagonist and the other ($C_2$) contains $C_1$ plus a 100-fold excess of unlabeled PAF, were also prepared and incubated simultaneously with the test samples. After the incubation was completed, the contents of each test tube were filtered under vacuo through a Whatman GF/C fiberglass filter and the residue washed rapidly several times with a total of 20 ml cold (0°-5° C.) Tris-buffer solution. Each washed residue was then suspended in 10 ml scintillation solution (Aquasol 2, New England Nuclear, Conn.) and the radioactivity was counted in a Packard Tri-Carb 460CD Liquid Scintillation System. Defining the counts from a test sample as "Total binding with antagonist"; the counts from the control sample $C_1$, as "Total binding $C_1$"; and the counts from the control sample $C_2$ as "non-specific binding $C_2$", the percent inhibition of each test antagonist can be determined by the following equations:

$$\% \text{ Inhibition} = \frac{(\text{Total binding } C_1) - \text{Total binding with antagonist}}{\text{Specific binding}} \times 100$$

Specific binding = (Total binding $C_1$) − (non-specific binding $C_2$)

The tested compounds of formula (I) inhibit in vitro PAF-induced platelet aggregation (rabbit or human platelets); PAF-induced guinea pig peritoneal PMN (polymorphonuclear leukocytes) aggregation; PAF-induced human PMN secretion; and PAF-induced guinea pig smooth muscle contraction although they are not $H_2$-receptor antagonists. They are also shown in these inhibition studies to be highly specific to PAF. For example, they do not inhibit the binding of $H_1$ antagonist ($^3$H-pyrilamine) to guinea pig brain membrane, nor do they inhibit the binding of a cholecystokinin (CCK) receptor based on an assay on isolated rat pancreas membrane. Furthermore, they affect no or only minute inhibition on the histamine-induced ileum contraction from guinea pigs.

The antagonistic activity of representative compounds of structural formula (I) in the trans configuration is summarized in the following tables.

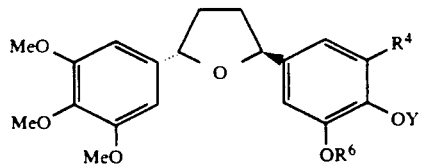

| $R^4$ | Y | $R^6$ | % Inhibition* |
|---|---|---|---|
| $SO_2CH_2COCH_3$ | $-CH_2CH_2CH_3$ | $-CH_2CH_2CH_2$-1-morpholine | 31 |
| $SO_2CH_2COCH_3$ (2S,5S) | $-CH_2CH_2CH_3$ | $-CH_2CH_2CH_2$-1-morpholine | 41 |
| $SO_2CH_2CH(OH)CH_3$ | $-CH_2CH_2CH_3$ | $-CH_2CH_2CH_2$-1-morpholine | 18 |
| $SO_2CH_2COCH_3$ | $-CH_2CH_2CH_3$ | $-CH_2CH_2$-1-morpholine | 25 |
| $SO_2CH_2COCH_3$ | $-CH_2CH_2CH_3$ | $-(CH_2)_4$-1-morpholine | 30 |
| $SO_2CH_2COCH_3$ | $-CH_2CH_2CH_3$ | $-(CH_2)_2$-1-piperizine | 34 |
| $SO_2CH_2COCH_3$ | $-CH_2CH_2CH_3$ | $-(CH_2)_2$-1-pyrrolidine | 29 |
| $SO_2CH_2COCH_3$ | $-CH_2CH_2CH_3$ | $-(CH_2)_3$-t-pyrrolidine | 48 |
| $SO_2CH_2COCH_3$ | $-CH_2CH_2CH_3$ | $-(CH_2)_2$-1-piperidine | 34 |
| $SO_2CH_2CH(OH)CH_3$ | $-CH_2CH_2CH_3$ | $-CH_2CH_2$-1-morpholine | 20 |
| $SO_2CH_2COCH_3$ | $-CH_2CH_2CH_3$ | $-(CH_2)_3$-1-imidazole | 56 |
| $SO_2CH_2COCH_3$ (2S,5S) | $-CH_2CH_2CH_3$ | $-(CH_2)_3$-1-imidazole | 74 |
| $SO_2CH_2COCH_3$ | $-CH_2CH_2CH_3$ | $-(CH_2)_3$-3-pyridine | 62 |
| $SO_2CH_2COCH_3$ | $-CH_2CH_2CH_3$ | $-(CH_2)_3$—S-3-triozole | 69 |
| $SO_2CH_2CH(OH)CH_3$ | $-CH_2CH_2CH_3$ | $-(CH_2)_3$—S-3-triozole | 61 |
| $SO_2CH_2CH(OH)CH_3$ | $-CH_2CH_2CH_3$ | $-(CH_2)_2$-1-imidazole | 48 |
| $SO_2CH_2CH(OH)CH_3$ | $-CH_2CH_2CH_3$ | $-(CH_2)_3$-1-imidazole | 41 |
| $SO_2CH_2CH(OH)CH_3$ | $-CH_2CH_2CH_3$ | $-(CH_2)_4$-1-imidazole | 43 |
| $SO_2CH_2CH(OH)CH_3$ | $-CH_2CH_2CH_3$ | $-(CH_2)_2$—S-2-imidazole | 34 |
| $SO_2CH_2CH(OH)CH_3$ | $-CH_2CH_2CH_3$ | $-(CH_2)_3$—S-2-imidazole | 46 |
| $SO_2CH_2COCH_3$ | $-CH_2CH_2CH_3$ | $-(CH_2)_2$—S-2-imidazole | 55 |
| $SO_2CH_2COCH_3$ | $-CH_2CH_2CH_3$ | $-(CH_2)_3$—S-2-imidazole | 45 |
| $SO_2CH_2COCH_3$ | $-CH_2CH_2CH_3$ | $-(CH_2)_4$—S-2-imidazole | 60 |
| $SO_2CH_2CH_2CH_3$ | $-(CH_2)_2$—S—$C_6H_4$-4-N(CH$_3$)$_2$ | $-CH_3$ | 66 |

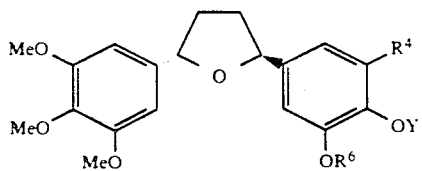

| R⁴ | Y | R⁶ | % Inhibition* |
|---|---|---|---|
| SO₂CH₂CH₂CH₃ | —(CH₂)₂—S—C₆H₄-4-OH | —CH₃ | 60 |
| SO₂CH₂CH₂CH₃ | —(CH₂)₂—S—C₆H₄-4-OH | —CH₃ | 100 |
| SO₂CH₂CH₂CH₃ | —(CH₂)₂—S-4-pyridine | —CH₃ | 73 |
| SO₂CH₂CH₂CH₃ | —(CH₂)₂—S—C₆H₄—CN | —CH₃ | 93 |
| SO₂CH₂CH₂CH₃ | —(CH₂)₂—S—C₆H₄-C(=NH)NH₂.HCl | —CH₃ | 60 |
| SO₂CH₂CH₂CH₃ | —(CH₂)₂—S—C₆H₄-2-tetrozole | —CH₃ | 52 |
| SO₂CH₂CH₂CH₃ | —(CH₂)₂—S-2-imidazole | —CH₃ | 60 |
| SO₂CH₂CH₂CH₃ | —(CH₂)₂—S-3-triozole | —CH₃ | 23 |
| SO₂CH₂CH₂CH₃ | —(CH₂)₂—SO₂—C₆H₅ | —CH₃ | 73 |
| SO₂CH₂CH₂-1-pyrrolidine | CH₂CH₂CH₃ | —CH₂CH₂CH₃ | 18 |
| SO₂CH₂CH₂-1-morpholine | CH₂CH₂CH₃ | —CH₂CH₂CH₃ | 17 |
| SO₂CH₂CH₂CH₃ | —(CH₂)₆—OH | —(CH₂)₂-1-morpholine | 55 |
| SO₂CH₂CH₂CH₃ | —(CH₂)₆—OH | —(CH₂)₃-1-morpholine | 48 |
| SO₂CH₂CH₂CH(OH)CH₃ | CH₂CH₂CH₃ | —(CH₂)₃-1-morpholine | 25 |
| SO₂CH₂CH(OH)CH₃ | CH₂CH₂CH₃ | —(CH₂)₂-2-imidazole | |

*% Inhibition of the binding of [³H] N-methylcarbamoyl-PAF to human platelet membranes at a drug concentration of 3 nM The following examples illustrate the preparation of representative compounds of this invention and pharmaceutical compositions thereof and as such are not to be considered as limiting the invention set forth in the claims appended hereto.

EXAMPLE 1

(−)-(2S,5S)-[3-(2-Oxopropylsulfonyl)-4-n-propoxy-5-{3-(1-morpholino)-n-propoxy}phenyl]-5-(3,4,5-trimethoxyphenyl)tetrahydrofuran

STEP A

3-Methylthio-4-hydroxy-5-benzyloxybenzaldehyde

A five liter flask equipped with a mechanical stirrer was charged with 100 g of 3-bromo-4-hydroxy-5-benzyloxybenzaldehyde, 80 g Cu powder, 80 mL methyldisulfide and 1.7 L pyridine, and the mixture was heated at 90° C. overnight with gentle stirring. The following day, the reaction mixture was filtered and most of the pyridine (1.3 L) was distilled off. The remaining solid residue was washed with about 2 L of methylene chloride and combined with the residue left after pyridine evaporation. The combined organic fraction was washed with 1.5N HCl until the dark methylene chloride layer turned light brown and the aqueous layer was clear. The resulting light brown methylene chloride layer was dried over MgSO₄ and filtered through a bed of silica gel. Evaporation and crystallization from methylene chloride-hexane gave the title compound: NMR (200 MHz, CDCl₃) 2.50 (s, SCH₃), 5.20 (s, OCH₂Ar), 6.72 (s, OH), 7.34–7.46 (m, ArH), 9.78 (s, ArCHO).

STEP B

3-Methylthio-4-n-propoxy-5-benzyloxybenzaldehyde 64.5 g of 3-methylthio-4-hydroxy-5-benzyloxybenzaldehyde dissolved in a 75 mL of DMF was treated with 50 g of K₂CO₃ and 32 g of 1-bromopropane and stirred overnight at 70° C. The next day about 1.5 liters of methylene chloride and an equal amount of water was added to the reaction mixture. The organic layer was removed, washed three times with distilled water, dried over MgSO₄ and evaporated to yield the title compound as viscous liquid that solidified slowly: NMR (200 MHz, CDCl₃) δ 1.02 (t, CH₂CH₂CH₃), 1.82 (m, CH₂CH₂CH₃), 2.48 (s, SCH₃), 4.12 (t, OCH₂CH₃), 5.18 (s, OCH₂Ar), 7.26–7.52 (m, ArH), 9.86 (s, ArCHO).

STEP C 1-(3-Methylthio-4-n-propoxy-5-benzyloxyphenyl)-4-(3,4,5-trimethoxyphenyl)butan-1,4-dione 175 g 3-methylthio-4-n-propoxy-5-benzyloxybenzaldehyde, 135 g of 3,4,5-trimethoxyphenylvinylketone, 10 g of 3-ethyl-5-(2-hydroxyethyl)-4-methylthiazolium-bromide, 25 mL of triethyl amine dissolved in 150 l of dimethylformamide was heated at 60° C. overnight, and the reaction mixture was treated with 400 mL of 1.5N HCl and the aqueous layer decanted. The residue was treated again with fresh 400 mL of 1.5N HCl and decanted two more times. The remaining residue was crystallized from 400 mL of methanol and washed thoroughly with methanol, hexane, and methanol and dried to yield the title compound as a tan solid: NMR (200 MHz, CDCl₃) δ 1.03 (t, CH₂CH₂CH₃), 1.82 (m, CH₂CH₂CH₃), 2.50 (s, SCH₃), 3.43 (s, C(O)CH₂CH₂CO), 3.94 (s, 3 OCH₃), 4.11 (t, OCH₂CH₂CH₃), 5.17 (s, OCH₂Ar), 7.30–7.52 (m, ArH).

STEP D 1-(3-Methylsulfonyl-4-n-propoxy-5-benzyloxyphenyl)-4-(3,4,5-trimethoxyphenyl)butan-1,4-dione 21.2 g of 1-(3-methylthio-4-propoxy-5-benzyloxyphenyl)-4-(3,4,5-trimethoxyphenyl)butan-1,4-dione dissolved in 350 mL of methylene chloride was cooled in ice bath and treated with 16 g of mCPBA (80%) in small portions. After 2–3 h of stirring, the mixture was cooled to 0° C., filtered to remove 3-chlorobenzoic acid and evaporated to a small volume. The residue obtained as such was taken up in ethyl acetate, washed with aqueous NaOH, water brine, dried over MgSO₄ and evaporated. The residue was crystallized from methanol to give the title compound: NMR (200 MHz, CDCl₃) δ0.99 (t, CH₂CH₂CH₃), 1.85 (m, CH₂CH₂CH₃), 3.30 (s, SO₂CH₃), 3.45 (s, C(O)CH₂CH₂CO), 3.93 (s, 3 OCH₃), 4.26 (t, OCH₂CH₂CH₃), 5.20 (s, OCH₂Ar), 7.29

(s, 4-ArH), 7.36–7.48 (m, ArH), 7.92 δ 8.25 (2 d, 1H each, 1-ArH).

STEP E (−)-(1S)-1-(3-Methylsulfonyl-4-n-propoxy-5-benzyloxyphenyl)-4-(3,4,5-trimethoxyphenyl) butan-1-ol-4-one A solution of 4.1 mL ethanol in 41 mL of THF was added dropwise to a stirred solution of 69 mL of 1N lithium aluminum hydride in tetrahydrofuran. After 15 min, a solution of 20.06 g of (S)-(−)-binaphthol in 180 mL of THF was added dropwise over a period of 2 h while maintaining the temperature of the milky mixture below 30° C. After stirring for additional 30 min at room temperature, the reaction mixture was cooled to −78° C., and a solution of 16 g of 1-(3-methylsulfonyl-4-n-propoxy-5-benzyloxyphenyl)-4-(3,4,5-trimethoxyphenyl) butan-1,4-dione (STEP D) in 125 mL THF was added dropwise to the mixture over a period of 1 h and stirring continued for 1–1.5 h. The reaction mixture was quenched with 28 mL of methanol and then concentrated in vacuo to remove THF and methanol. The residue was taken up in ethyl acetate and the organic phase was washed with 1N HCl, water, brine and concentrated in vacuo. The (−)-binaphthol was precipitated with methylene chloride/hexane.

The procedure described in the preceeding paragraph was repeated with another 16 g of 1-(3-methylsulfonyl-4-n-propoxy-5-benzyloxyphenyl)-4-(3,4,5-trimethoxy-phenyl) butan-1,4-dione, and the concentrated filtrates obtained after precipitation of (−)-binaphthol were combined, chromatographed on silica column (hexane/ethyl acetate), and crystallized from methylene chloride-hexane to yield the title compound as a glassy solid: $[\alpha]_3 = -10.1$; NMR (200 MHz, CDCl$_3$) δ 0.98 (t, CH$_2$CH$_2$CH$_3$), 1.82 (m, CH$_2$CH$_2$CH$_3$), 2.04–2.24 (m, CH$_2$CHOH), 3.10 (t, C(O)CH$_2$CH$_2$CHOH, 3.26 (s, SO$_2$CH$_3$), 3.94 (s, 3 OCH$_3$), 4.16 (t, OCH$_2$CH$_2$CH$_3$), 4.85 (m, CH$_2$CHOH), 5.16 (s, OCH$_2$Ar), 7.23 (s, 4-ArH), 7.30–7.52 (m, ArH).

STEP F (−)-(1S)-1-(3-Methylsulfonyl-4-n-propoxy-5-benzyloxyphenyl)-4-(3,4,5-trimethoxyphenyl) butan-1,4-diol 35 g of (−)-(1S)-1-(3-methylsulfonyl-4-n-propoxy-5-benzyloxyphenyl)-4-(3,4,5-trimethoxyphenyl) butan-1-ol-4-one (STEP E) dissolved in a mixture of 300 mL dry THF and 100 mL of methanol was treated with 3.5 g of NaBH$_4$ at 0° C. and stirred for 3 h. The reaction mixture was then allowed to gradually warm to room temperature and stirring was continued for additional 2 h. After the completion of the reaction, the solvent was evaporated at reduced pressure and the residue obtained as such was redissolved in 300 ml of ethyl acetate. The organic layer was washed with 1.5N HCl, distilled water and brine respectively, and then dried over MgSO$_4$ and evaporated to yield a colorless syrup which was used without further purification.

STEP G 1-(3-Methylsulfonyl-4-n-propoxy-5-benzyloxyphenyl)-4-(3,4,5-trimethoxyphenyl)butan-1,4-diol This compound was prepared from 1-(3-methylsulfonyl-4-n-propoxy-5-benzyloxyphenyl)-4-(3,4,5-trimethoxyphenyl) butan-1,4-dione (STEP D) as shown for (−)-(1S)-1-(3-methylsulfonyl-4-n-propoxy-5-benzyloxyphenyl)-4-(3,4,5-trimethoxyphenyl) butan-1-ol-4-one (STEP F) and used without further purification.

STEP H (−)-trans-(2S,5S)-2-(3-Methylsulfonyl-4-n-propoxy-5-benzyloxyphenyl)-5-(3,4,5-trimethoxyphenyl)tetrahydrofuran 37 g of (−)-(1S)-1-(3-methylsulfonyl-4-n-propoxy-5-benzyloxyphenyl) -4-(3,4,5-trimethoxyphenyl)butan-1,4-diol (STEP F) dissolved in 185 mL of chloroform (stabilized with ethanol) was treated dropwise with 10% TFA in chloroform and stirred for 16 h at 0° C. The reaction mixture was washed with 5% NaOH, water, brine, dried over MgSO$_4$ and evaporated to yield 35.1 g of colorless syrup. It was then separated on a silica column (30% ethyl acetate in hexane) into cis and trans isomers. The trans isomer was crystallized from ether: $[\alpha]_D - 62.4$; NMR (200 MHz, CDCl$_3$) δ 0.98 (t, CH$_2$CH$_2$CH$_3$), 1.82 (m, CH$_2$CH$_2$CH$_3$), 1.9–2.6 (m, 3-CH$_2$ δ 4-CH$_2$), 3.27 (s, SO$_2$CH$_3$), 3.85 (s, OCH$_3$), 3.94 (s, 2 OCH$_3$), 4.16 (t, CCH$_2$CH$_2$CH$_3$), 5.17 (s, OCH$_2$Ar), 5.06–5.28 (m, 2-CH δ 5-CH), 6.61 (s, 5-ArH), 7.28–7.54 (m, ArH).

STEP I racemic trans-2-(3-Methylsulfonyl-4-n-propoxy-5-benzyloxyphenyl)-5-(3,4,5-trimethoxyphenyl) tetrahydrofuran This compound was prepared from 1-(3-methylsulfonyl-4-n-propoxy-5-Benzyloxyphenyl)-4-93,4,5-trimethoxyphenyl)butan-(1,4-diol (STEP G) as shown above in STEP H).

STEP J trans-2-[3-(2-Oxopropylsulfonyl)-4-n-propoxy-5-benzyloxyphenyl]-5-(3,4,5-trimethoxyphenyl) tetrahydrofuran 2.7 g trans-2-(3-methylsulfonyl-4-n-propoxy-5-benzyloxyphenyl)-5-(3,4,5-trimethoxyphenyl) tetrahydrofuran (STEP I) dissolved in 15 mL THF was cooled to −78° and treated with 5.3 mL of 1.6M n-BuLi. After about 5 minutes of stirring, to the resulting dark solution, 1.0 mL of acetic anhydride was added. The yellow reaction mixture was allowed to warm up to room temperature and treated with 3–4 g of solid ammonium chloride, water and ether. NMR showed that the desired ketosulfone has formed to the extent of 80%. The ether layer was separated, dried over NaSO$_4$, evaporated and chromatographed over silica (20% ethyl acetate in hexane) to yield the title compound after crystallization from ether: NMR (200 MHz, CDCl$_3$) δ 0.98 (t, CH$_2$CH$_2$CH$_3$), 1.83 (m, CH$_2$CH$_2$CH$_3$), 1.9–2.6 (m, 3-CH$_2$ δ4-CH$_2$), 2.38 (s, CH$_3$C(O)CH$_2$), 3.86 (s, OCH$_3$), 3.88 (s, 2 OCH$_3$), 4.18 (t, OCH$_2$CH$_2$CH$_3$), 4.48 (s, CH$_3$C(O)CH$_2$), 5.18 (s, OCH$_2$Ar), 5.06–5.28 (m, 2-CH δ 5-CH), 6.61 (s, 5-ArH), 7.32–7.54 (m, ArH).

STEP K (−)-trans-(2S,5S)-2-[3-(2-Oxopropylsulfonyl)-4-n-propoxy-5-benzyloxyphenyl)-5-(3,4,5-trimethoxyphenyl) tetrahydrofuran This compound was prepared from (−)-trans-(2S,5S)-2-(3-methylsulfonyl-4-n-propoxy-5-benzyloxyphenyl) -5-(3,4,5-trimethoxyphenyl) tetrahydrofuran as shown above in the racemic case (STEP J).

STEP L trans-2-[3-(2-Oxopropylsulfonyl)-4-n-propoxy-5-hydroxyphenyl]-5-(3,4,5-trimethoxyphenyl)tetrahydrofuran A mixture of 1.2 g of 2-[3-(2-oxopropylsulfonyl)-4-n-propoxy-5-benzyloxyphenyl]-5-(3,4,5-trimethoxyphenyl) tetrahydrofuran (STEP J), 400 mg 10% PD/C, 1-2 drops of acetic acid in 100 mL of ethyl acetate was stirred under $H_2$ at 40 psi for 45 minutes. The reaction mixture was filtered over a bed of celite and evaporated in vacuo to yield the title compound: NMR (200 MHz, $CDCl_3$) δ 1.10 (t, $CH_2CH_2CH_3$), 1.92 (m, $CH_2CH_2CH_3$), 1.9–2.6 (m, 3-$CH_2$ δ 4-$CH_2$), 2.40 (s, $CH_3C(O)CH_2$), 3.86 (s, $OCH_3$), 3.90 (s, 2 $OCH_3$), 4.12 (t, $CH_2CH_2CH_3$), 4.42 (s, $CH_3C(O)CH_2$), 5.10–5.28 (m, 2-CH δ 5-CH), 6.64 (s, 5-ArH), 7.35 δ 7.47 (2 d, 2-ArH).

STEP M trans-(−)-(2S,5S)-[3-(2-Oxopropylsulfonyl)-4-n-propoxy-5-hydroxyphenyl]-5-(3,4,5-trimethoxyphenyl)tetrahydrofuran This compound was prepared from (−)-trans-(2S,5S)-2-[3-(2-oxopropylsulfonyl)-4-n-propoxy-5-benzyloxyphenyl]-5-(3,4,5-trimethoxyphenyl) tetrahydrofuran (STEP K) as shown above in the racemic case STEP L: NMR (200 MHz, $CDCl_3$) δ 1.10 (t, $CH_2CH_2CH_3$), 1.92 (m, $CH_2CH_2CH_3$), 1.9–2.6 (m, 3-$CH_2$ δ 4-$CH_2$), 2.40 (s, $CH_3C(O)CH_2$), 3.86 (s, $OCH_3$), 3.90 (s, 2 $OCH_3$), 4.12 (t, $OCH_2CH_2CH_3$), 4.42 (s, $CH_3C(O)CH_2$), 5.10–5.28 (m, 2-CH δn 5-CH), 6.64 (s, 5-ArH), 7.35 δ 7.47 (2 d, 2-ArH).

STEP N trans(−)-(2S,5S)-[3-(2-Oxopropylsulfonyl)-4-n-propoxy-5-{3-(1-morpholino)-n-propoxy}phenyl]-5-(3,4,5-trimethoxyphenyl)tetrahydrofuran A mixture of 300 mg of (−)-(2S,5S)-[3-(2-oxopropylsulfonyl)-4-n-propoxy-5-hydroxyphenyl]-5-(3,4,5-trimethoxyphenyl) tetrahydrofuran (STEP M), 6 mL acetone, 150 mg 3-bromopropylmorpholine hydrochloride, and 150 mg $K_2CO_3$ was heated at 50° for 16 hrs and filtered. Evaporation of the filtrate and purification by prep. TLC on silica plates (ethyl acetate) gave the title compound as a colorless gum: $[\alpha]_D$ −57.8°; NMR (200 MHz, $CDCl_3$) δ 1.06 (t, $CH_2CH_2CH_3$), 1.88 (m, $CH_2CH_2CH_3$), 1.9–2.6 (m, 3-$CH_2$ δ 4-$CH_2$), 2.38 (s, $CH_3C(O)CH_2$), 2.40–2.66 (m, $CH_2N[(CH_2)_2]_2$, 3.75 (br t, $CH_2OCH_2$), 3.85 (s, $OCH_3$), 3.88 (s, 2 $OCH_3$), 4.13 δ 4.14 (2 t, $ArOCH_2$), 4.46 (s, $CH_3C(O)CH_2$), 5.10–5.30 (m, 2-CH δ 5-CH), 6.62 (s, 5-ArH), 7.30 δ 7.45 (2 d, 2-ArH).

STEP O trans-2-[3-(2-oxopropylsulfonyl)-4-n-propoxy-5-{3-(1-morpholino)-n-propoxy}phenyl]-5-(3,4,5-trimethoxyphenyl)tetrahydrofuran The title compound was prepared from 2-[3-(2-oxopropylsulfonyl)-4-n-propoxy-5-hydroxyphenyl]-5-(3,4,5-trimethoxyphenyl) tetrahydrofuran (STEP L) by the methods outlined in STEP N. NMR was the same as the chiral compound.

EXAMPLE 2 trans-(2S,5S)-[3-(2-hydroxypropylsulfonyl)-4-n-propoxy-5-{3-(1-morpholino)-n-propoxy}phenyl]-5-(3,4,5-trimethoxyphenyl)tetrahydrofuran Reduction of 80 mg of trans-(2S,5S)-[3-(2-oxopropylsulfonyl)-4-n-propoxy-5-{3-(1-morpholino)-n-propoxy}phenyl]-5-(3,4,5-trimethoxyphenyl)tetrahydrofuran (Example 1, Step N) in 2 mL methanol and 40 mg of sodium borohydride gave the title compound after the usual workup: NMR (200 MHz, $CDCl_3$) δ 1.04 (t, $CH_2CH_2CH_3$), 1.24 (d, $CH_2CH(OH)CH_3$), 1.87 (m, $CH_3CH_2CH_2$), 1.9–2.6 (m. 3-$CH_2$ δ 4-$CH_2$), 2.70 (m, $CH_2N[(CH_2)_2]_2$, 3.4–3.64 (m, $CH(OH)CH_2SO_2$), 3.74 (br t, $CH_2OCH_2$), 3.86 (s, $OCH_3$), 3.88 (s, 2 $OCH_3$), 4.10 δ 4.12 (2 t, $ArOCH_2$), 5.14–5.26 (m, 2-CH δ 5-CH), 6.63 (s, 5-ArH), 7.30 δ 7.50 (2 dd, 2-ArH).

EXAMPLE 2A trans-(2S,5S)-[3-(2-Hydroxypropylsulfonyl)-4-n-propoxy-5-{3-(1-morpholino)-n-propoxy}phenyl]-5-(3,4,5-trimethoxyphenyl)tetrahydrofuran Preparation of the chiral enantiomers

STEP A trans-(2S,5S)-2-[3-(2-Hydroxypropylsulfonyl)-4-n-propoxy-5-benzyloxyphenyl)-5-(3,4,5-trimethoxyphenyl) tetrahydrofuran The title compound as a racemic mixture of alcohols was prepared from (−)-trans-(2S,5S)-2-[3-(2-oxopropylsulfonyl)-4-n-propoxy-5-benzyloxyphenyl)-5-(3,4,5-trimethoxyphenyl) tetrahydrofuran by reduction in methanol with excess sodium borohydride according to procedures described in Example 2. The NMR was the same as for Example 17.

STEP B

Resolution of trans-(2S,5S)-2-[3-(2-Hydroxypropylsulfonyl)-4-n-propoxy-5-benzyloxyphenyl)-5-(3,4,5-trimethoxyphenyl)tetrahydrofuran 0.28 gm of the title compound was combined with 0.09 gm (R)-(−)-3-O-metylman- delic acid, 0.1 gm of 1-ethyl-3-(3-dimethyaminopropyl) carbodiimide (EDAC), and 1 crystal of 4-dimethylamino- pyridine in 5 ml of methylene chloride. After stirring at room temperature for 1 hour the reaction mixture was diluted with ethyl acetate, washed with water and brine, dried over $MgSO_4$ and evaporated to give an oil that was chromatographed on silica gel eluting with methylene chloride:hexanes:ethyl acetate, 50:35:15 to give the separate enantiomers. The ester groups were removed liberating the free alcohols by reduction of the esters in THF at 0° C. with lithium aluminumhydride. The crude products were isolated by chromatography through a short column of silica gel.

STEP C trans-(2S,5S)-2-[3-(2-Hydroxypropylsulfonyl)-4-n-propoxy-5-{3-(1-morpholino)-n-propoxy}phenyl]-5-(3,4,5-trimethoxyphenyl)tetrahydrofuran Preparation of the chiral enantiomers The title enantiomers were prepared from appropriate starting materials according to procedures outlined in Examples 18, and 1, step N.

More Polar Enantiomer: NMR (CDCl$_3$) δ 1.05 (t, CH$_2$CH$_2$CH$_3$), 1.24 (d, CH(OH)CH$_3$), 1.86 (m, CH$_2$CH$_2$CH$_3$), 1.9-2.6 (m, C-3CH$_2$, C-4CH$_2$), 2.47 (m, CH$_2$N(CH$_2$CH$_2$)$_2$O), 3.4-3.6 (m, CH(OH)CH$_2$SO$_2$), 3.74 (m, CH$_2$N(CH$_2$CH$_2$)$_2$O), 3.86 (s, OCH$_3$), 3.88 (s, OCH$_3$), 4.11 (m, 2ArOCH$_2$), 5.14-5.26 (m, C-2H, C-5H), 6.63 (s, 5ArH), 7.11 (d.2ArH), 7.30 (m, ArH)

Less Polar Enantiomer: NMR (CDCl$_3$) δ 1.05 (t, CH$_2$CH$_2$CH$_3$), 1.24 (d, CH(OH)CH$_3$), 1.86 (m, CH$_2$CH$_2$CH$_3$), 1.9-2.6 (m, C-3CH$_2$, C-4CH$_2$), 2.47 (m, CH$_2$N(CH$_2$CH$_2$)$_2$O), 3.4-3.6 (m, CH(OH)CH$_2$SO$_2$), 3.74 (m, CH$_2$N(CH$_2$CH$_2$)$_2$O), 3.86 (s, OCH$_3$), 3.88 (s, OCH$_3$), 4.11 (m, 2ArOCH$_2$), 5.14-5.26 (m, C-2H, C-5H), 6.63 (s, 5ArH), 7.08 (d.2ArH), 7.30 (m, ArH).

The following compounds were prepared from the appropriate starting materials by the procedures as outlined in Examples 1 and 2.

EXAMPLE 3 trans-2-[3-(2-Oxopropylsulfonyl)-4-n-propoxy-5-{2-(1-morpholino)-ethoxy}phenyl]-5-(3,4,5-trimethoxyphenyl)tetrahydrofuran NMR (200 MHz, CDCl$_3$) δ 1.06 (t, CH$_2$CH$_2$CH$_3$), 1.88 (m, CH$_2$CH$_2$CH$_3$), 1.9-2.6 (m, 3-CH$_2$ δ 4-CH$_2$), 2.38 (s, CH$_3$C(O)CH$_2$), 2.60 (m, N[(CH)$_2$]$_2$, 2.86 (t, OCH$_2$CH$_2$N), 3.74 (br t, CH$_2$OCH$_2$), 3.86 (s, OCH$_3$), 3.89 (s, 2 OCH$_3$), 4.18 δ 4.19 (2 t, ArOCH$_2$), 4.46 (s, CH$_3$C(O)CH$_2$), 5.10-5.30 (m, 2-CH δ 5-CH), 6.62 (s, 5-ArH), 7.32 δ 7.46 (2 d, 2-ArH).

EXAMPLE 4 trans-2-[3-(2-Oxopropylsulfonyl)-4-n-propoxy-5-{3-(1-piperizinyl)-n-propoxy}phenyl]-5-(3,4,5-trimethoxyphenyl)tetrahydrofuran NMR (200 MHz, CDCl$_3$) δ 1.06 (t, CH$_2$CH$_2$CH$_3$), 1.88 (m, CH$_2$CH$_2$CH$_3$), 1.9-2.6 (m, 3-CH$_2$ δ 4-CH$_2$), 2.36 (s, CH$_3$C(O)CH$_2$), 2.60 (m, CH$_2$N(CH$_2$)$_2$, 3.85 (s, OCH$_3$), 3.88 (s, 2 OCH$_3$), 4.04-4.24 (m, 2 ArOCH$_2$), 4.46 (s, CH$_3$C(O)CH$_2$), 5.10-5.30 (m, 2-CH δ 5-CH), 6.62 (s, 5-ArH), 7.30 δ 7.45 (2 d, 2-ArH).

EXAMPLE 5 trans-2-[3-(2-Oxopropylsulfonyl)-4-n-propoxy-5-{2-(1-piperidinyl)-ethoxy}phenyl]-5-(3,4,5-trimethoxyphenyl)tetrahydrofuran NMR (200 MHz, CDCl$_3$) δ 1.06 (t, CH$_2$CH$_2$CH$_3$), 1.36-1.5 (m, piperidine 4-CH), 1.5-1.7 (m, piperidine 3-CH δ 4-CH), 1.88 (m, CH$_2$CH$_2$CH$_3$), 1.9-2.6 (m, 3-CH$_2$ δ 4-CH$_2$), 2.38 (s, CH$_3$C(O)CH$_2$), 2.74 (m, N[(CH)$_2$]$_2$, 2.82 (t, OCH$_2$CH$_2$N), 3.85 (s, OCH$_3$), 3.88 (s, 2 OCH$_3$), 4.08 δ 4.24 (m, 2 ArOCH$_2$), 4.46 (s, CH$_3$C(O)CH$_2$), 5.10-5.30 (m, 2-CH δ 5-CH), 6.62 (s, 5-ArH), 7.30 δ 7.45 (2 d, 2-ArH).

EXAMPLE 6 trans-2-[3-(2-Oxopropylsulfonyl)-4-n-propoxy-5-{4-(1-morpholino)-n-butoxy}phenyl]-5-(3,4,5-trimethoxyphenyl)tetrahydrofuran NMR (200 MHz, CDCl$_3$) δ 1.08 (t, CH$_2$CH$_2$CH$_3$), 1.88 (m, CH$_2$CH$_2$CH$_3$), 2.38 (s, CH$_3$C(O)CH$_2$), 3.64 (br t, CH$_2$OCH$_2$), 3.86 (s, OCH$_3$), 3.89 (s, 2 OCH$_3$), 4.44 (s, CH$_3$C(O)CH$_2$), 5.10-5.30 (m, 2-CH δ 5-CH), 6.62 (s, 5-ArH), 7.43 δ 7.50 (2 d, 2-ArH).

EXAMPLE 7 trans-2-[3-(2-Oxopropylsulfonyl)-4-n-propoxy-5-{2-(1-pyrrolidino)-ethoxy}phenyl]-5-(3,4,5-trimethoxyphenyl)tetrahydrofuran NMR (200 MHz, CDCl$_3$) δ 1.06 (t, CH$_2$CH$_2$CH$_3$), 2.38 (s, CH$_3$C(O)CH$_2$), 2.68 (m, CH$_2$N(CH$_2$), 3.00 (t, CH$_2$N(CH$_2$), 3.86 (s, OCH$_3$), 3.89 (s, 2 OCH$_3$), 4.1-4.26 (m, ArOCH$_2$), 4.46 (s, CH$_3$C(O)CH$_2$), 5.10-5.30 (m, 2-CH δ 5-CH), 6.63 (s, 5-ArH), 7.34 δ 7.46 (2 d, 2-ArH).

EXAMPLE 8 trans-2-[3-(2-Oxopropylsulfonyl)-4-n-propoxy-5-{3-(1-pyrrolidino)-n-propoxy}phenyl]-5-(3,4,5-trimethoxyphenyl)tetrahydrofuran NMR (200 MHz, CDCl$_3$) δ 1.06 (t, CH$_2$CH$_2$CH$_3$), 2.38 (s, CH$_3$C(O)CH$_2$), 2.62 (t, OCH$_2$CH$_2$CH$_2$N), 3.86 (s, OCH$_3$), 3.89 (s, 2 OCH$_3$), 4.16 (t, 2 ArOCH$_2$), 4.47 (s, CH$_3$C(O)CH$_2$), 5.10-5.30 (m, 2-CH δ 5-CH), 6.63 (s, 5-ArH), 7.32 δ 7.46 (2 d, 2-ArH).

EXAMPLE 9 trans-2-[3-(2-Hydroxypropylsulfonyl)-4-n-propoxy-5-{2-(1-morpholino)-n-ethoxy}phenyl]-5-(3,4,5-trimethoxyphenyl)tetrahydrofuran NMR (200 MHz, CDCl$_3$) δ 1.06 (t, CH$_2$CH$_2$CH$_3$), 1.25 (d, CH$_2$CH(OH)CH$_3$), 1.90 (m, CH$_3$CH$_2$CH$_2$), 2.60 (br t, CH$_2$N(CH$_2$)$_2$), 2.86 (t, CH$_2$N(CH$_2$)$_2$), 3.4-3.64 (m, CH(OH)CH$_2$SO$_2$), 3.74 (br t, CH$_2$OCH$_2$), 3.86 (s, OCH$_3$), 3.88 (s, 2 OCH$_3$), 4.10-4.28 (t, 2 ArOCH$_2$), 5.14-5.26 (m, 2-CH δ 5-CH), 6.63 (s, 5-ArH), 7.30 δ 7.52 (2 dd, 2-ArH).

EXAMPLE 10 trans-2-[3-(2-Hydroxypropylsulfonyl)-4-n-propoxy-5-{3-(1-piperidinyl)-n-propoxy}phenyl]-5-(3,4,5-trimethoxyphenyl)tetrahydrofuran NMR (CDCl$_3$) δ 2.58 (m, CH$_2$NHCH$_2$), 3.04 (CH$_2$N(CH$_2$)$_2$), 3.90 (S, OCH$_3$), 3.94 (S, 2-OCH$_3$), 4.16 (m, Ar-OCH$_2$), 5.22 (m, 2-CH, 5-CH), 6.62 (5-ArH), 7.3-7.5 (2-Ar-H).

EXAMPLE 11 trans-2-[3-(2-Oxopropylsulfonyl)-4-n-propoxy-5-(w-bromoalkoxy)phenyl]-5-(3,4,5-trimethoxyphenyl)tetrahydrofuran Dibromoalkane (100 uL) was added to a solution of trans-2-[3-(2-oxopropylsulfonyl)-4-n-propoxy-5-(hydroxy)phenyl]-5-(3,4,5-trimethoxyphenyl) tetrahydrofuran (100 mg) [Example 1, Step L] in acetone (100 mL) containing K$_2$CO$_3$ (100 mg), and the mixture was heated at 50° C. for 16 h and filtered. The filtrate was concentrated to a residue, which was purified by preparative TLC (hexaneethyl acetate; 3:2, v/v) to give the desired products.

The following compounds were prepared from the appropriate starting materials by the procedures as outlined in Example 11.

EXAMPLE 11A trans-2-[3-(2-Oxopropylsulfonyl)-4-n-propoxy-5-(2-bromoethoxy)phenyl]-5-(3,4,5-trimethoxyphenyl) tetrahydrofuran NMR (CDCl$_3$) δ 1.1 (t, CH$_2$CH$_2$CH$_3$), 1.85 (m, CH$_2$CH$_2$CH$_3$), 2.0 δ 2.49 (2 m, H-3 δ H-4), 2.4 (s, CH$_2$COCH$_3$), 3.7 (t, CH$_2$CH$_2$Br), 3.81 δ 3.86 (2 s, 3 OCH$_3$), 4.2 (t, CH$_2$CH$_2$Br), 4.4 (t, CH$_2$CH$_2$CH$_3$), 4.46 (s, CH$_2$COCH$_3$), 5.20 (2 m, H-2 δ H-5), 6.60 (s, C$_5$ArH), 7.22 δ 7.45 (2 d, J = 1.5 Hz, C$_2$ArH).

EXAMPLE 11B trans-2-[3-(2-Oxopropylsulfonyl)-4-n-propoxy-5-(3-bromopropoxy)phenyl]-5-(3,4,5-trimethoxyphenyl) tetrahydrofuran NMR (CDCl$_3$) δ NMR (CDCl$_3$) δ 1.1 (t, CH$_2$CH$_2$CH$_3$), 1.84 (m, CH$_2$CH$_2$CH$_3$) 1.94 (m, CH$_2$CH$_2$CH$_2$), 2.0 δ 2.49 (2 m, H-3 δ H-4), 2.4 (s, CH$_2$COCH$_3$), 3.7 (2 t, CH$_2$Br), 3.81 δ 3.86 (2 s, 3 OCH3), 4.14 (t, CH$_2$CH$_2$CH$_2$Br), 4.25 (t, CH$_2$CH$_2$CH$_3$), 4.46 (s, CH$_2$CO), 5.20 (m, H-2 δn H-5), 6.60 (s, C$_5$ArH), 7.36 δ 7.50 (2 d, J = 1.5 Hz, C$_2$ArH).

EXAMPLE 11C trans-2-[3-(2-Oxopropylsulfonyl)-4-n-propoxy-5-(4-bromobutoxy)phenyl]-5-(3,4,5-trimethoxyphenyl) tetrahydrofuran NMR (CDCl$_3$) δ 1.08 (t, CH$_2$CH$_2$CH$_3$), 1.84 (m, CH$_2$CH$_2$CH$_3$) 1.94 (m, CH$_2$CH$_2$CH$_2$), 2.0 δ 2.49 (2 m, H-3 δ H-04), 2.05 (m, CH$_2$CH$_2$CH$_2$CH$_2$), 2.4 (s, CH$_2$COCH$_3$), 3.5 (t, CH$_2$Br), 3.81 δ 3.86 (2 s, 3 OCH$_3$), 4.1 (m, CH$_2$CH$_2$CH$_2$CH$_2$Br & CH$_2$CH$_2$CH$_3$), 4.46 (s, CH$_2$CO), 5.20 (m, H-2 & H-5), 6.60 (s, C$_5$ArH), 7.24 & 7.43 (2 d, J = 1.5 Hz, C$_2$ArH).

EXAMPLE 12 trans-2-[3-(2-Oxopropylsulfonyl)-4-n-propoxy-5-{3-(1-imidazolyl)n-propoxyl}phenyl]-5-(3,4,5)-trimethoxyphenyl)tetrahydrofuran A mixture of trans-2-[3-(2-oxopropylsulfonyl)-4-propoxy-5-(3-bromopropoxy)phenyl]-5-(3,4,5-trimethoxyphenyl) tetrahydrofuran (70 mg) (Example 11B), imidazole (70 mg) and K$_2$CO$_3$ (70 mg) in acetone (5ml) was heated with stirring at 50° C. for 96 h. The mixture was filtered and the filtrate was concentrated to a residue, which was purified by preparative TLC (chloroform-methanol-water; 90:10:1, v/v) to give the title compound: R$_f$ 0.4; MS, m/z 616 M$^+$; NMR (CDCl$_3$): δ 1.09 (t, CH$_2$CH$_2$CH$_3$), 1.90 (m, CH$_2$CH$_2$CH$_3$), 1.94 (m, CH$_2$CH$_2$CH$_2$CH$_2$), 2.0 & 2.49 (2 m, H-3 & H-4), 2.3 (m, CH$_2$CH$_2$CH$_2$), 2.4 (s, CH$_2$COCH$_3$), 3.84 & 3.88 (2 s, 3 OCH$_3$), 4.05 (t, CH$_2$CH$_2$CH$_3$), 4.2 (m, OCH$_2$CH$_2$CH$_2$N), 4.5 (s, CH$_2$CO), 5.2 (m, H-2 & H-5), 6.62 (s, C$_5$ArH), 6.95, 7.1 & 7.55 (3 s, imidazole), 7.23 & 7.5 (2 d, J = 1.5 Hz, C$_2$ArH).

EXAMPLE 13 trans-(2S,5S)-2-[3-(2-Oxopropylsulfonyl)-4-n-propoxy-5-{3-(1-imidazolyl)propoxy}phenyl]-5-(3,4,5-trimethoxyphenyl)tetrahydrofuran This compound was prepared from trans-(2S,5S)-2-[3-(2-oxopropylsulfonyl)-4-n-propoxy-5-(3-bromopropoxy)phenyl]-5-(3,4,5-trimethoxyphenyl)tetrahydrofuran [which was prepared from (−)-2(S)-[5-hydroxy-3-(2-oxopropylsulfonyl)-4-n-propoxyphenyl]-5(S)-(3,4,5-trimethoxyphenyl)tetrahydrofuran(Example 1, Step M) which was alkylated with 1,3-dibromopropane according to Example 11B] and imidazole in a similar manner as described above for the racemate. The title compound had [α]$_D$−58° (c 1.0, CHCl$_3$).

EXAMPLE 14 trans-2-{3-(2-Oxopropylsulfonyl)-4-n-propoxy-5-[3-(3-pyridyl)propoxy}phenyl]-5-(3,4,5-trimethoxyphenyl) tetrahydrofuran 3-(3-Bromopropyl)pyridine hydrobromide (51 mg, 0.18 mmol) was added to a solution of trans-2-[3-(2-oxopropylsulfonyl)-4-n-propoxy-5-(2-hydroxy)phenyl]-5-(3,4,5-trimethoxyphenyl) tetrahydrofuran (50.8 mg, 0.1 mmol) [Example 1, Step L] in DMF (2 mL) containing postassium carbonate (28 mg, 0.2 mmol), and the reaction mixture was heated at 70° C. for 1 h. The product was extracted with ethyl ether in the usualy way and purified by preparative TLC (hexane-ethyl acetate; 1.2, v/v) R$_f$ 0.15; MS, m/z 628 (M + 1)$^+$; NMR (CDCl$_3$)δ d 1.09 (t, J = 7.5 Hz, CH$_2$CH$_2$CH$_3$), 1.92 (m, CH$_2$CH$_2$CH$_3$), 2.18 (m, CH$_2$CH$_2$CH$_2$Pyr), 2.37 (s, CH$_2$COCH$_3$), 2.87 (T, CH$_2$CH$_2$CH$_2$Pyr), 3.83 (s, OCH$_3$), 3.88 (s, 2 OCH$_3$), 4.08 (t, CH$_2$CH$_2$CH$_2$Pyr), 4.18 (t, CH$_2$CH$_2$CH$_3$), 4.48 (s, CH$_2$CO), 5.13–5.27 (m, H-2 & H-5), 6.61 (s, 2 H, C$_5$ArH).

EXAMPLE 15 trans-2-[3-(2-Oxopropylsulfonyl)-4-n-propoxy-5-{3-(1H-1,2,4-triazolyl-3-thio)n-propoxy}phenyl]-5-(3,4,5-trimethoxyphenyl)tetrahydrofuran

STEP 15A trans-2-[3-(2-Oxopropylsulfonyl)-4-n-propoxy-5-(3-hydroxy-n-propoxy)phenyl]-5-(3,4,5-trimethoxyphenyl) tetrahydrofuran A mixture of trans-2-[3-(2-oxopropylsulfonyl)-4-propoxy-5-hydroxyphenyl]-5-(3,4,5-trimethoxyphenyl)-tetrahydrofuran (30 mg, 0.059 mmol), 3-bromo-1-propanol (12 uL, 0.13 mmol) and potassium carbonate (17 mg, 0.12 mmol) in DMF (0.5 mL) was heated at 80° C. with stirring under nitrogen for 1 h. The reaction mixture was cooled and diluted with ethyl ether. It was washed with water (2x), brine, dried, filtered, and evaporated to a residue, which was purified by preparative TLC (hexane-ethyl acetate; 7:3, v/v) to give the title compound: R$_f$ 0.3; NMR (CDCl$_3$) δ 2.38 (s, SO$_2$CH$_2$COCH$_3$), 4.15 & 4.24 (2 t, OCH$_2$CH$_2$), 4.48 (s, SO$_2$CH$_2$), 5.22 (m, H-2 & H-5).

STEP 15B trans-2-[3-(2-Oxopropylsulfonyl)-4-n-propoxy-5-{3-(1H-1,2,4-triazolyl-3-thio)propoxy}phenyl]-5-(3,4,5-trimethoxyphenyl)tetrahydrofuran Methanesulfonyl chloride (0.03 mL, 0.38 mmol) was added to a stirred solution of trans-2-[3-(2-oxopropylsulfonyl)4-n-propoxy-5-(3-hydroxy-n-propoxy)phenyl]-5-(3,4,5-trimethoxyphenyl)tetrahydrofuran (143 mg, 0.25 mmol) in dry pyridine ((0.5 mL) at 0° C. under nitrogen. After 90 min, a small amount of ice was added and the reaction mixture was stirred at room temperature for another 30 min. Ethyl acetate as added and the organic layer was washed with 2N HCl (2×), 10% NaHCO$_3$ and brine, dried, and evaporated to give the mesylate intermediate (158 mg, 98%) as a colorless foam: R$_f$ 0.5 (hexane-ethyl acetate; 3:7, v/v); NMR (CDCl$_3$)δ 2.38 (CH$_2$COCH$_3$), 3.04 (OSO$_2$CH$_3$). A mixture of the above mesylate (155 mg, 0.24 mmol), sodium iodie (0.19 g, 1.26 mmol) in ethyl methyl ketone (2 mL) was heated with stirring at 80° C. under nitrogen for 75 min. The solvent was evaporated and the residue was partitioned between ethyl ether and water. The ethereal layer was washed with sodium thiosulfate and water, dried, and evaporated to give the iodo derivative (140 mg. 86%): $R_f$ 0.75 (hexane-ethyl acetate; 1:1, v/v); NMR (CDCl$_3$) δ 2.38 (CH$_2$COCH$_3$), 3.40 (CH$_2$I), 4.48 (CH$_2$CO). Sodium hydride (4 mg, 0.1 mmol; 60% suspension in mineral oil) was added to a stirred solution of 1H-1,2,4-triazole-3-thiol (11 mg, 0.11 mmol) in DMF (0.25 mL) at room temperature under nitrogen. After 5 min, a solution the iodo derivative (67 mg, 0.1 mmol) in DMF (0.75 mL) was added and the mixture was stirred for 1 h. Ethyl acetate-ether (1:1) and water were added and the organic layer was washed water and brine, dried, and evaporated to a residue. Purification by preparative TLC (CH$_2$Cl$_2$-MeOH; 9:1, v/v) gave the title compound as a colorless foam: $R_f$ 0.6; MS, m/z 649 M+; NMR (CDCl$_3$) δ 2.36 (s, CH$_2$COCH$_3$), 3.34 (b, CH$_2$S), 4.48 (s, CH$_2$COCH$_3$), 7.98 (s, triaz-CH).

EXAMPLE 16 trans-2-[3-(2-Hydroxy-n-propylsulfonyl)-4-n-propoxy-5-{3-(1H-1,2,4-triazolyl-3-thio)propoxy}phenyl]-5-(3,4,5-trimethoxyphenyl)tetrahydrofuran A mixture of trans-2-[3-(2-oxopropylsulfonyl)-4-n-propoxy-5-{3-(1H-1,2,4-triazolyl-3-thio)propoxy}phenyl]-5-(3,4,5-trimethoxyphenyl)tetrahydrofuran (20 mg, 0.03 mmol) [Example 15] and sodium borohydrate (3 mg, 0.08 mmol) in ethanol (0.5 mL) was heated at 60° C. under nitrogen for 1 h. The mixture was diluted with CH$_2$Cl$_2$ (2mL) and water (2 mL) and made neutral with 1N HCl. The organic layer was separated and washed with water and brine, dried, and evaporated to a residue (21 mg). Purification by preparative TLC (CH$_2$Cl$_2$-MeOH; 92:8, v/v) gave the title compound as a colorless foam; $R_f$ 0.6 (CH$_2$Cl$_2$-MeOH; 9:1, v/v); NMR (CDCl$_3$) δ 1.25 (d, CH$_2$CHOHCH$_3$).

EXAMPLE 17 trans-2[-3-(2-Hydroxy-n-propylsulfonyl)-4-n-propoxy-5-(2-benzyloxy)phenyl]-5-(3,4,5-trimethoxyphenyl)tetrahydrofuran Acetaldehyde (0.7 mL, 12.4 mmol) was added under nitrogen to a solution of trans-2-[3-methylsulfonyl-4-n-propoxy-5-(2-benzyloxy) phenyl]-5-(3,4,5-trimethoxyphenyl)tetrahydrofuran (1.15 g, 2.07 mmol) (Example 1, Step I) and LDA (2.5 mL, 2.5 mmol; 1.5M in cyclohexane) in THF (15 mL) at −70° C. The mixture was stirred at this temperature for 10 min, and then allowed to warm to room temperature. Dichloromethane was added and the solution was washed with aq. NH$_4$Cl, dried, and evaporated to dryness. The residue was purified by flash column chromatography (hexane-ethyl acetate; 2:1, v/v) to give the title compound as a crystalline mass: mp 103°-110° C.; $R_f$ 0.17 (s.m. had $R_f$ 0.27; hexane-ethyl acetate; 3:2, v/v); NMR (CDCl$_3$) δ 0.98 (t, J=7.5 Hz, CH$_2$CH$_2$CH$_3$), 1.25 (d, J=6.5 Hz, CH$_2$CHOHCH$_3$), 3.86 (s, OCH$_3$), 3.89 (s, 2 OCH$_3$), 5.18 (s, CH$_2$Ph), 6.63 (s, 2 H, C$_5$ArH).

EXAMPLE 18 trans-2-[3-(2-Hydroxypropylsulfonyl)-4-n-propoxy-5-hydroxyphenyl]-5-(3,4,5-trimethoxyphenyl)tetrahydrofuran A solution of trans-2-[3-(2-hydroxy-n-propylsulfonyl)-4-n-propoxy-5-(2-benzyloxy)phenyl]-5-(3,4,5-trimethoxyphenyl) tetrahydrofuran (1.07 g, 1.78 mmol) (Example 17) in ethyl acetate (5 mL) was hydrogenated over 10% palladium-over-charcoal (200 mg) for 1 h. The catalyst was filtered off and washed with ethyl acetate. The filtrates were combined and evaporated to a syrup: NMR (CDCl$_3$) δ 1.08 (t, J=7.5 Hz, CH$_2$CH$_2$CH$_3$), 1.25 (d, J=6.5 Hz, CH$_2$CHOHCH$_3$), 3.86 (s, OCH$_3$), 3.88 (s, 2 OCH$_3$), 5.15-5.26 (m, H-2 & H-5), 6.62 (s, 2 H, C$_5$ArH), 7.34 & 7.50 (2 d,d, 2 H, C$_2$ArH).

EXAMPLE 19A trans-2-[3-(2-Hydroxy-n-propylsulfonyl)-4-n-propoxy-5-(2-bromoethoxy)phenyl]-5-(3,4,5-trimethoxyphenyl)tetrahydrofuran 1,2-Dibromoethane (1.12 mL, 13 mmol) was added to a solution of trans-2-[3-(2-hydroxy-n-propylsulfonyl)-4-n-propoxy-5-hydroxyphenyl]-5-(3,4,5-trimethoxyphenyl) tetrahydrofuran (331 mg, 0.65 mmol) (Example 18) in DMF (5 mL) containing potassium carbonate (550 mg, 3.9 mmol). The reaction mixture was heated with stirring at 70° C. for 7 h and, cooled, and partitioned between ethyl ether and water. The ethereal layer was separated and the aqueous layer was re-extracted twice with ether. The organic extracts were combined, dried, and evaporated to dryness. The product was purified by flash column chromatography on silica gel using hexane-ethyl acetate (2:1, v/v) as the eluant: $R_f$ 0.42 (hexane-ethyl acetate; 1:2, v/v); NMR (CDCl$_3$) δ 1.06 (t, CH$_2$CH$_2$CH$_3$), 1.25 (d, CH$_2$CHOHCH$_3$), 1.90 (m, CH$_2$CH$_2$CH$_3$), 3.74 (t, CH$_2$CH$_2$Br), 3.83 (s, OCH$_3$), 3.88 (s, 2 OCH$_3$), 5.16-5.28 (m, H-2 & H-5), 6.62 (s, 2 H, C$_5$ArH), 7.28 and 7.54 (2 d, 2 H, C$_2$ArH).

EXAMPLE 19B trans-2-[3-(2-Hydroxypropylsulfonyl)-4-n-propoxy-5-(3-bromo-n-propoxy)phenyl]-5 (3,4,5-trimethoxyphenyl) tetrahydrofuran 1,3-Dibromopropane (0.105 mL, 1.0 mol) was added to a solution of trans-2-[3-(2-hydroxypropylsulfonyl)-4-n-propoxy-5-hydroxyphenyl]-5-(3,4,5-trimethoxyphenyl)tetrahydrofuran (102 mg, 0.20 mmol) in DMF (1 mL) containing potassium carbonate (105 mg, 0.76 mmol). The reaction mixture was heated with stirring under nitrogen at 70° C. for 2 h, cooled, and partitioned between ethyl ether and water. The ethereal layer was separated and the aqueous layer was re-extracted twice with ether. The organic extracts were combined, dried, and evaporated to a residue (143 mg). Purification by preparative TLC (hexane-ethyl acetate; 1:1, v/v) gave the title compound as a colorless foam; $R_f$ 0.5; NMR (CDCl$_3$) δ 1.26 (d, CH$_2$CHOHCH$_3$), 3.66 (t, CH$_2$Br).

EXAMPLE 19C trans-2-[3-(2-Hydroxy-n-propylsulfonyl)-4-n-propoxy-5-(4-bromobutoxy)phenyl]-5-(3,4,5-trimethoxyphenyl)tetrahydrofuran 1,4-Dibromobutane (75 uL, 0.63 mmol) was added to a solution of trans-2-[3-(2-hydroxy-n-propylsulfonyl)-4-n-propoxy-5-hydroxyphenyl]-5-(3,4,5-trimethoxyphenyl)tetrahydrofuran (75 mg, 0.15 mmol) in DMF (0.5 mL) containing potassium carbonate (75 mg, 0.54 mmol). The reaction mixture was heated with stirring under nitrogen at 70° C. for 1.5 h, cooled, and partitioned between ethyl ether and water. The ethereal layer was separated and the aqueous layer was re-extracted twice with ether. The organic extracts were combined, dried, and evaporated to a residue. Purification by preparative TLC (hexane-ethyl acetate; 1:1, v/v) gave the title compound as a colorless viscous oil: $R_f$ 0.5; NMR (CDCl$_3$) δ 1.25 (d, CH$_2$CHOHC̲H̲$_3$).

EXAMPLE 20 trans-2-[3-(2-Hydroxy-n-propylsulfonyl-4-n-propoxy-5-{2-(1-imidazolyl)ethoxy}phenyl]-5-(3,4,5-trimethoxyphenyl)tetrahydrofuran A mixture of trans-2-[3-(2-hydroxy-n-propylsulfonyl)-4-n-propoxy-5-(2-bromoethoxy)phenyl]-5-(3,4,5-trimethoxyphenyl) tetrahydrofuran (45 mg, 0.073 mmol) (Example 19A), imidazole (25 mg, 0.36 mmol) and potassium carbonate (50 mg, 0.36 mmol) in acetone (2 mL) was heated with stirring at 55° C. under nitrogen for 42 h. The reaction mixture was evaporated and the residue was partitioned between dichloromethane and water. The organic layer was washed with water and brine, dried, and evaporated to a residue. Purification by preparative TLC (CH$_2$Cl$_2$-MeOH; 9:1, v/v) gave the title compound: $R_f$ 0.5; MS, m/z, 604 M$^+$·; NMR (CDCl$_3$) δ 7.06 (bd, NCH=CHN), 7.76 (bs, NCH=N).

EXAMPLE 21 trans-2-[3-(2-Hydroxy-n-propylsulfonyl)-4-n-propoxy-5-{3-(1-imidazolyl)propoxy}phenyl]-5-(3,4,5-trimethoxyphenyl)tetrahydrofuran A mixture of trans-2-[3-(2-hydroxy-n-propylsulfonyl)-4-n-propoxy-5-(3-bromopropoxy)phenyl]-5-(3,4,5-trimethoxyphenyl) tetrahydrofuran (87 mg, 0.14 mmol) (Example 19B), imidazole (47 mg, 0.69 mmol) and potassium carbonate (95 mg, 0.69 mmol) in acetone (2 mL) was heated with stirring at 55° C. under nitrogen for 28 h. The reaction mixture was evaporated and the residue was partitioned between dichloromethane and water. The organic layer was washed with water and brine, dried, and evaporated to a residue. Purification by preparative TLC (CH$_2$Cl$_2$-MeOH; 9:1, v/v) gave the title compound: $R_f$ 0.6; MS, m/z 618 M$^+$·; NMR (CDCl$_3$)δ 1.28 (bd, CH$_2$CHOHC̲H̲$_3$). 6.94 & 7.08 (bs, NCH=CHN), 7.54 (NCH=N).

EXAMPLE 22 trans-2-[3-(2-Hydroxy-n-propylsulfonyl)-4-n-propoxy-5-{4-(1-imidazolyl)butoxy}phenyl]-5-(3,4,5-trimethoxyphenyl)tetrahydrofuran A mixture of trans-2-[-3-(2-hydroxy-n-propylsulfonyl)-4-n-propoxy-5-(4-bromobutoxy)phenyl]-5-(3,4,5-trimethoxyphenyl) tetrahydrofuran (64 mg, 0.10 mmol)-(Example 19C), imidazole (27 mg, 0.40 mmol) and potassium carbonate (55 mg, 0.40 mmol) in acetone (3 mL) was heated with stirring at 60° C. under nitrogen for 24 h. The reaction mixture was evaporated and the residue was partitioned between dichloromethane and water. The organic layer was washed with water and brine, dried, and evaporated to a residue. Purification by preparative TLC (CH$_2$Cl$_2$-MeOH; 92.8, v/v) gave the title compound: $R_f$ 0.5; MS, m/z 632 M$^+$·; NMR (CDCl$_3$) δ 1.28 (bd, CH$_2$CHOHC̲H̲$_3$), 6.94 & 7.08 (bs, NCH=CHN).

EXAMPLE 23 trans-2-[3-(2-Hydroxy-n-propylsulfonyl)-4-n-propoxy-5-{2-(2-imidazolylthio)ethoxy}phenyl]-5-(3,4,5-trimethoxyphenyl)tetrahydrofuran A solution of trans-2-[3-(2-hydroxy-n-propylsulfonyl)-4-propoxy-5-(2-bromoethoxy)phenyl]5-(3,4,5-trimethoxyphenyl) tetrahydrofuran (47 mg, 0.07 mmol)-(Example 19A) in DMF (250 mL) was added to a mixture of 2-mercaptoimidazole (25 mg, 0.25 mL) and NaH (56%; 10 mg, 0.25 mmol) in DMF (0.5 mL) under nitrogen, and the mixture was stirred at room temperature for 30 min. Water (5 mL) and ethyl ether (5 mL) were added, and the mixture was stirred for another 5 min. The ethereal layer was separated, dried over MgSO$_4$, and filtered. The filtrate was evaporated to a residue, which was purified by preparative TLC (EtOAc) to give the title compound: $R_f$ 0.5; MS m/z 636 M$^+$·; NMR (CDCl$_3$) δ 1.02 (t, CH$_2$CH$_2$C̲H̲$_3$), 1.24 (d, CH$_2$CHOHC̲H̲$_3$), 1.85 (m, CH$_2$C̲H̲$_2$CH$_3$), 2.0 & 2.49 (2 m, H-3 & H̲-4), 3.42 (m, CH$_2$S), 3.54 (m, C̲H̲$_2$CHOH) 3.84 & 3.88 (2 s, 3 OCH$_3$), 4.18 (m, C̲H̲$_2$C̲H̲$_2$S), 4.3 (m, CH$_2$C̲H̲OH), 4.38 (t, C̲H̲$_2$CH$_2$CH$_3$), 5.22 (m, H-2 & H̲-5), 6.62 (s, C$_5$ArH), 6.96 (s, NH), 7.1 (s, imidazole), 7.32 & 7.50 (2 d, J=1.5 Hz, C$_2$ArH).

EXAMPLE 24 trans-2-[3-(2-Hydroxy-n-propylsulfonyl)-4-n-propoxy-5-{3-(2-imidazolylthio)n-propoxy}phenyl]-5-(3,4,5-trimethoxyphenyl)tetrahydrofuran This compound was prepared from the appropriate starting materials according to the method as outlined in Example 23: MS, m/z 651 M$^+$·; NMR (CDCl$_3$) δ1.02 (t, CH$_2$CH$_2$C̲H̲$_3$), 1.24 (d, CHOHC̲H̲$_2$CH$_3$), 1.85 (m, CH$_2$C̲H̲$_2$CH$_3$), 2.0 & 2.49 (2m, H-3 & H̲-4), 2.2 (m, CH$_2$C̲H̲$_2$CH$_2$), 3.2 (m, CH$_2$S), 3.5 (m, C̲H̲$_2$CHOH), 3.84 & 3.88 (2 s, 3 OCH$_3$), 4.1 (m, OCH$_2$C̲H̲$_2$CH$_2$S), 4.2 (t, C̲H̲$_2$CH$_2$CH$_3$), 4.22 (m, CH$_2$C̲H̲OH), 5.22 (m, H-2 & H̲-5), 6.62 (s, C$_5$ArH), 6.96 (s, NH), 7.05 (s, imidazole), 7.3 & 7.50 (2 d, J=1.5 Hz, C$_2$ArH).

EXAMPLE 25 trans-2-[3-(2-Hydroxy-n-propylsulfonyl)-4-n-propoxy-5-{3-(phenylaminopropoxy}phenyl]-5-(3,4,5-trimethoxyphenyl)tetrahydrofuran This compound was prepared according to the procedure outlined in Example 22 using aniline in place of imidazole.

The compounds of Examples 26 and 28 as prepared from the appropriate starting materials according to the method as outlined in Example 23.

EXAMPLE 26 trans-2-[3-(2-Oxopropylsulfonyl)-4-n-propoxy-5-{2-(2-imidazolylthio)ethoxy}phenyl]-5-(3,4,5-trimethoxyphenyl)tetrahydrofuran MS, m/z 634 M$^+$·; NMR (CDCl$_3$): δ 1.02 (t, CH$_2$CH$_2$C̲H̲$_3$), 1.85 (m, CH$_2$C̲H̲$_2$CH$_3$), 1.94 (m, CH$_2$C̲H̲$_2$CH$_2$), 2.0 & 2.49 (2 m, H̲-3 & H-4), 2.4 (s, COC̲H̲$_3$), 3.2 (m, CH$_2$S), 3.84 & 3.88 (2 s, 3 OCH$_3$), 4.1 (t, C̲H̲$_2$CH$_2$CH$_3$), 4.4 (t, OCH$_2$C̲H̲$_2$S), 4.46 (s, COCH$_2$), 5.22 (m, H-2 & H-5), 6.62 (s, C̲$_5$ArH), 7.1 (s, imidazole), 7.32 & 7.44 (2 d, J=1.5 Hz, C$_2$ArH).

EXAMPLE 27 trans-2-[3-(2-Oxopropylsulfonyl)-4-n-propoxy-5-{3-(2-imidazolylthio)propoxy}phenyl]-5-(3,4,5-trimethoxyphenyl)tetrahydrofuran MS, m/z 648 M$^+$·; NMR (CDCl$_3$) δ 1.02 (t, CH$_2$CH$_2$C̲H̲$_3$), 1.85 (m, CH$_2$C̲H̲$_2$CH$_3$), 1.94 (m, CH$_2$C̲H̲$_2$CH$_2$), 2.0 & 2.49 (2 m, H̲-3 & H-4), 2.4 (s, CH$_2$COC̲H̲$_3$), 3.2 (m, CH$_2$S), 3.84 & 3.88 (2s, 3 OCH$_3$), 4.1 (t, C̲H̲$_2$CH$_2$CH$_3$), 4.2 (t, OC̲H̲$_2$ CH$_2$CH$_2$S), 4.46 (s, CH$_2$CO), 5.22 (m, H-2 & H-5), 6.62 (s, C$_5$ArH), 7.1 (s, imidazole), 7.32 & 7.44 (2 d, J=1.5 Hz, C$_2$ArH).

EXAMPLE 28 trans-2-[3-(2-Oxopropylsulfonyl)-4-n-propoxy-5-{4-(2-imidazolylthio)butoxy}phenyl]-5-(3,4,5-trimethoxyphenyl)tetrahydrofuran NMR (CDCl$_3$) δ 1.02 (t, CH$_2$CH$_2$CH$_3$), 1.85 (m, CH$_2$CH$_2$CH$_3$), 1.94 (m, CH$_2$CH$_2$CH$_2$CH$_2$), 2.0 2.49 (2 m, H-3 & H-4), 2.4 (s, CH$_2$COCH$_3$), 3.15 (t, CH$_2$SO, 3.84 & 3.88 (2 s, 3 OCH$_3$), 4.1 (2 t, CH$_2$CH$_2$CH$_3$ & OCH$_2$CH$_2$CH$_2$), 4.48 (s, CH$_2$CO), 5.22 (m, H-2 & H-5), 6.62 (s, C$_5$ArH), 7.05 (s, imidazole), 7.28 & 7.45 (2 d, J=1.5 Hz, C$_2$ArH).

EXAMPLE 29 trans-2-[3-(2-Hydroxy-n-propylsulfonyl)-4-n-propoxy-5-{2-(2-thiazolyl)ethoxy}phenyl]-5-(3,4,5-trimethoxyphenyl)tetrahydrofuran trans-2-[3-(2-Hydroxy-n-propylsulfonyl)-4-n-propoxy-5-(2-bromoethoxy) phenyl]-5-(3,4,5-trimethoxyphenyl)tetrahydrofuran (50 mg, 0.08 mmol)(Example 12) was converted into the corresponding iodide by treatment with sodium iodide in DMF. The iodo intermediate and thiazole (0.17 mL, 2.4 mmol) in toluene (5 mL) was heated under reflux overnight. The solution was evaporated to dryness, and the product was isolated by preparative TLC (chloroform-methanol; 9:1, v/v), R$_f$0.08.

EXAMPLE 30 trans-2-[3-n-Propylsulfonyl-4-{2-(4-dimethylaminophenylthio)ethoxy}-5-methoxyphenyl]-5-(3,4,5-trimethoxyphenyl)tetrahydrofuran

STEP 30A

3-Iodo-4-benzyloxy-5-methoxybenzoldehyde

Benzyl chloride (30 g, 0.24 mol) was added to a solution of 5-iodovanillin (60 g, 0.216 mol) in DMF (250 mL), containing potassium carbonate (50 g). The mixture was stirred at 80° for 1.5 h or until TLC (hexane-ethyl acetate; 4:1, v/v; R$_f$0.5) showed the reaction to be complete. The mixture was then cooled and the solvent was decanted into ice-water (1 L). The product was extracted with ethyl ether and the ethereal layer was washed with water, dried, and evaporated in vacuo to an oil, which solidified upon standing: mp 53°-54° C.

STEP 30B 1-(3-Iodo-4-benzyloxy-5-methoxyphenyl)-4-(3,4,5-trimethoxyphenyl)-1,4-butanedione A solution of 3-iodo-4-benzyl-oxy-5-methoxybenzaldehyde (69 g, 0.19 mol) in DMF (150 mL) was added to a suspension of sodium cyanide (3 g) in DMF (50 mL). A solution of the Mannich base (46 g, 0.18 mol) in DMF (150 mL) was added immediately, and the mixture was stirred at room temperature for 1.5 h or until the reaction was complete as monitored by TLC (hexane-ethyl acetate; 3:1, v/v; R$_f$0.22). The orange mixture was poured onto 2.5N HCl and ice (2 L), and the precipitate was filtered and dried by suction. (If the solid was gummy, it was taken up in CH$_2$Cl$_2$ and washed with water, dried, filtered, and the filtrate was evaporated to dryness.) Recrystallization from ethyl ether afforded pure product: mp 134°-135° C.

STEP 30C 1-(3n-Propylthio-4-benzyloxy-5-methoxyphenyl)-4-(3,4,5-trimethoxyphenyl)-1,4-butanedione A mixture of 1-(3-iodo-4-benzyloxy-5-methoxyphenyl)-4-(3,4,5-trimethoxyphenyl)-1,4-butanedione (50 g), n-propyldisulfide (50 mL) and copper powder (50 g) in DMF (300 mL) was heated under reflux for 24 h, cooled, and filtered over celite. The filtrate was concentrated to dryness and the residue was taken up in CH$_2$Cl$_2$ and washed with water, dried, and evaporated to dryness. Crystallization from ethyl ether afforded pure produce, mp 114°-115° C.

STEP 30D 1-(3-n-Propylsulfonyl-4-benzyloxy-5-methoxyphenyl)-b 4-93,4,5-trimethoxyphenyl)-1,4-butanedione 3-Chloroperoxybenzoic acid (80%; 14 g) was added to a solution of 1-(3-n-propylthio-4-benzyloxy-5-methoxyphenyl)- 4-(3,4,5-trimethoxyphenyl)-1,4-butanedione (16.5 g) in dichloromethane (200 mL), and the mixture was stirred at room temperature for 3 h. The solid was filtered off and the filtrate was concentrated to a small volume. Ethyl ether was added top give crystals: mp 148°-150° C.

STEP 30E trans-2-(3-Propylsulfonyl-4-benzyloxy-5-methoxyphenyl)-5-(3,4,5-trimethoxyphenyl)tetrahydrofuran A suspension of 1-(3-propylsulfonyl-4-benzyloxy-5-methoxyphenyl)-4-(3,4,5-trimethoxyphenyl)-1,4-butanedione (13.5 g) and NaBH$_4$ (1.5 g) in ethanol (170 mL) was heated with stirring at 70° C. for 1 h. The solvent was concentrated to dryness and the residue was taken up in dichloromethane and washed with water, dried, and evaporated to give the diol. Chloroform (90 mL) was added and the solution was cooled to 0° C., and 10% trifluroacetic acid in chloroform (90 mL) was added. The solution was allowed to stand for 3 h and Na$_2$CO$_3$ (50 g) was added and the mixture was stirred for 20 min. The solid was filtered and the filtrate was concentrated to dryness. The products were purified by HPLC (hexane-ethyl acetate; 3:1, v/v) to give the title compound and the corresponding cis-isomer. Recrystallization of the title compound from dichloromethane-ether gave pure material: MS, m/z 556 M$^+$; mp 176°-177° C.

STEP 30F trans-2-(3-n-Propylsulfonyl-4-hydroxy-5-methoxyphenyl)-5-(3,4,5-trimethoxyphenyl)tetrahydrofuran A solution of trans-2-(3-n-propylsulfonyl-4-benzyloxy-5-methoxyphenyl)-5-(3,4,5-trimethoxyphenyl) tetrahydrofuran (5.0 g) in ethyl acetate (100 mL) was hydrogenated over 10% palladium-over-charcoal (250 mg) for 1 h. The catalyst was filtered off and the filtrate was concentrated to a crystalline mass. Recrystallization from ethyl ether gave pure product: mp 168°-169° C.; NMR (CDCl$_3$) δ 1.0 (t, CH$_2$CH$_2$CH$_3$), 1.7 (m, CH$_2$CH$_2$CH$_3$), 2.0 & 2.49 (2 m, H-3 & H-4), 3.4 (m, CH$_2$CH$_2$CH$_3$), 3.84, 3.89 & 3.93 (3 s, 4 OCH$_3$), 5.20 (m, H-2 & H-5), 6.62 (s, C$_5$ArH), 7.24 & 7.47 (2 d, J=1.5 Hz, C$_2$ArH).

STEP 30G trans-2-[3-n-Propylsulfonyl-4-(2-bromoethoxy)-5-methoxyphenyl]-5-(3,4,5-trimethoxyphenyl)tetrahydrofuran A mixture of trans-2-(3-n-propylsulfonyl-4-hydroxy-5-methoxyphenyl)-5-(3,4,5-trimethoxyphenyl) tetrahydrofuran (4.66 g, 10 mmol), 1,2-dibromoethane (1.84 mL, 20.5, mmol) and $K_2CO_3$ (4.0 g) in DMF (20 mL) was heated with stirring at 80° C. for 1 h. The reaction mixture was cooled and partioned between ethyl ether and water. The organic layer was separated, dried, and evaporated to a crystalline mass. Recrystallization from ethyl ether-hexane afforded the title compound, mp 135°-136° C.

STEP 30H trans-2-[-3-n-Propylsulfonyl-4-{2-(4-Dimethylaminophenylthio)ethoxy}-5-methoxyphenyl}-5-(3,4,5-trimethoxyphenyl)tetrahydrofuran Trans-2-[3-n-propylsulfonyl-4-(2-bromoethoxy)-5-methoxyphenyl]-5-(3,4,5-trimethoxyphenyl)tetrahydrofuran (100 mg) (Step 30G) was added to a stirred solution of 4-dimethylaminothiophenol (76 mg, 0.5 mmol) and sodium hydride (56%; 20 mg, 0.5 mmol) in DMF (1 mL). The reaction mixture was stirred at room temperature for 20 min and partitioned between ethyl ether and water. The organic layer was separated, dried, and evaporated to a crystalline mass. Recrystalized from ethyl ether-hexane gave pure product: mp 113°-115° C.; NMR ($CDCl_3$) δ 1.0 (t, $CH_2CH_2\underline{CH_3}$), 1.70 (m, $CH_2\underline{CH_2}CH_3$), 2.0 & 2.49 (2 m, H-3 & H-4), 3.0 [m, $(CH_3)_2N$], 3.4 (m, $\underline{CH_2}CH_2CH_3$), 3.84 3.88 & 3.9 (3 s, 3 $OCH_3$), 4.30 (t, $S\underline{CH_2}CH_2O$), 5.22 (m, H-2 & H-5), 6.62 (s, $C_5ArH$), 7.23 & 7.47 (2 d, J=1.5 Hz, $C_2ArH$), 7.42 (m, ArH).

The compounds of Examples 31 to 34 were prepared from the appropriate starting materials according to the procedures as outlined in Example 30.

EXAMPLE 31 trans-2-[3-n-Propylsulfonyl-4-{2-(4-aminophenylthio)-ethoxy}-5-methoxyphenyl]-5-(3,4,5-trimethoxyphenyl) tetrahydrofuran MS, m/z 617 M⁻; NMR ($CDCl_3$) δ 0.98 (t, $CH_2CH_2\underline{CH_3}$), 1.70 (m, $CH_2\underline{CH_2}CH_3$), 1.97 & 2.47 (2 m, H-3 & H-4), 3.2 (t, $\underline{CH_2}CH_2S$), 3.36 (m, $CH_3CH_2\underline{CH_2}SO_2$) 3.82, 3.84 & 3.7 (3 s, 3 $OCH_3$), 4.24 (t, $SCH_2\underline{CH_2}O$), 5.22 (m, H-2 & H-5), 6.60 (s, $C_5ArH$), 6.61 7.3 (2 d, J=9.0 ArH), 7.2 & 7.44 (2 d, J=1.5 Hz, $C_2ArH$).

EXAMPLE 32 trans-2-[3-Propylsulfonyl-4-{2-(4-hydroxyphenylthio)-ethoxy}-5-methoxyphenyl]-5-(3,4,5-trimethoxyphenyl) tetrahydrofuran MS, m/z 618 M⁺; NMR ($CDCl_3$) δ 0.98 (t, $CH_2CH_2\underline{CH_3}$), 1.70 (m, $CH_2\underline{CH_2}CH_3$), 1.98 & 2.47 (2 m, H-3 & H-4), 3.2 (t, $CH_2\underline{CH_2}S$), 3.36 (m, $\underline{CH_2}CH_2CH_3$), 3.84, 3.86 & 3.88 (3 s, 3 $OCH_3$), 4.24 (t, $SCH_2\underline{CH_2}O$), 5.21 (m, H-2 & H-5), 6.60 (s, $C_5ArH$), 6.68 7.38 (2d,J=8.0 ArH), 7.23 & 7.46 (2 d, J=1.5 Hz, $C_2ArH$), 8.0 (s, ArOH).

EXAMPLE 33 trans-2-[3-n-Propylsulfonyl-4-{2-(4-pyridylthio)ethoxy}-5-methoxyphenyl]-5-(3,4,5-trimethoxyphenyl) tetrahydrofuran MS. m/z 604 M⁺; NMR ($CDCl_3$) δ 0.98 (t, $CH_2CH_2\underline{CH_3}$), 1.70 (m, $CH_2\underline{CH_2}CH_3$), 1.98 & 2.47 (2 m, H-3 & H-4), 3.36 (m, $\underline{CH_2}CH_2CH_3$), 3.45 (t, $CH_2\underline{CH_2}S$), 3.82, 3.87 & 3.89 (3 s, 3 $OCH_3$), 4.34 (t, $SCH_2\underline{CH_2}O$), 5.2 (m, H-2 & H-5), 6.60 (s, $C_5ArH$), 7.21 & 8.4 (2 d, PyrH), 7.26 & 7.47 (2 d, J=1.5 Hz, $C_2ArH$).

EXAMPLE 34 trans-2-[3-n-Propylsulfonyl-4-{2-(4-cyanophenylthio)ethoxy}-5-methoxyphenyl]-5-(3,4,5-trimethoxyphenyl) tetrahydrofuran MS, m/z 627 M⁺; NMR ($CDCl_3$) δ0.98 (t, $CH_2CH_2\underline{CH_3}$), 1.72 (m, $CH_2\underline{CH_2}CH_3$), 1.98 & 2.49 (2m, H-3 & H-4), 3.37 (m, $\underline{CH_2}CH_2CH_3$), 3.45 (t, $CH_2\underline{CH_2}S$), 3.84 3.86 & 3.89 (3 s, 3 $OCH_3$), 4.35 (t, $SCH_2\underline{CH_2}O$), 5.22 (m, H-2 & H-5), 6.62 (s, $C_5ArH$), 7.26 & 7.49 (2 d, J=1.5 Hz, $C_2ArH$), 7.42 & 7.56 (2 d, J=9.0 Hz, ArH).

EXAMPLE 35 trans-2-[3-n-Propylsulfonyl-4-{2-(4-amidinophenylthio)ethoxy}-5-methoxyphenyl]-5-(3,4,5-trimethoxyphenyl)tetrahydrofuran Sodium methoxide (0.54 mL of 54 mg/mL in MeOH) was added to a solution of trans-2-[3-n-propyl-sulfonyl-4-{2-(4-cyanophenylthio) ethoxy}-5-methoxyphenyl]-5-(3,4,5-trimethoxyphenyl) tetrahydrofuran (50 mg) in methanol (1 mL). This was followed by addition of $NH_4Cl$ (20 mg), and the reaction mixture was stirred at room temperature for 1 h. The solvent was evaporated and the residue was purified by preparative TLC (EtOAc) to give the title compound: MS, m/z 645 (M+1)⁺; NMR ($CDCl_3$) δ 0.98 (t, $CH_2CH_2\underline{CH_3}$), 1.66 (m, $CH_2\underline{CH_2}CH_3$), 1.98 & 2.49 (2m, H-3 & H-4), 3.36 (m, $\underline{CH_2}CH_2CH_3$), 3.44 (t, $CH_2\underline{CH_2}S$), 3.83, 3.88 & 3.93 (3 s, 3 $OCH_3$), 4.26 (t, $SCH_2\underline{CH_2}O$), 5.22 (m, H-2 & H-5), 6.62 (s, $C_5ArH$), 7.26 & 7.46 (2 d, J=1.5 Hz, $C_2ArH$), 7.40 & 7.80 (2 d, J=8 Hz, ArH).

EXAMPLE 36 trans-2-[3-n-Propylsulfonyl-4-{2-(4-(2-tetrazo) phenylthio)ethoxy}-5-methoxyphenyl]-5-(3,4,5-trimethoxyphenyl)tetrahydrofuran A mixture of trans-2-[3-n-propylsulfonyl-4-{2-(4-cyanophenylthio) ethoxy}-5-methoxyphenyl]-5-(3,4,5-trimethoxyphenyl) tetrahydrofuran (100 mg) and $NaN_3$ (50 mg) in DMF (1 mL) was heated with stirring at 50° C. for 5 h, cooled, and partitioned between $Et_2O$ and water. The organic layer was dried and evaporated to a residue, which was purified by preparative TLC to give the title compound: MS, m/z 671 (M+1)³⁰⁻.

EXAMPLE 37 trans-2-[3-n-Propylsulfonyl-4-{2-(2-imidazolthio) ethoxy}-5-methoxyphenyl]-5-(3,4,5-trimethoxyphenyl) tetrahydrofuran This compound was prepared similarly as described before: MS, m/z 592 M³⁰⁻; NMR ($CDCl_3$) δ1.04 (t, $CH_2CH_2\underline{CH_3}$), 1.80 (m, $CH_2\underline{CH_2}CH_3$), 1.98 & 2.49 (2 m, H-3 & H-4), 3.24 (t, $\underline{CH_2}CH_2S$), 3.68 (m, $\underline{CH_2}CH_2CH_3$), 3.84, 3.86 & 3.89 (3 s, 3 $OCH_3$), 4.26 (t, SCH$_2$CH$_2$O), 5.22 (m, H-2 & H-5), 6.62 (s, C$_5$ArH), 7.12 (s, imidazole), 7.3 & 7.56 (2 d, J=1.5 Hz, C$_2$ArH).

EXAMPLE 38 trans-2-[3-n-Propylsulfonyl-4-{2-(3-triazolthio) ethoxy}-5-methoxyphenyl]-5-(3,4,5-trimethoxyphenyl) tetrahydrofuran This compound was prepared similarly as described above: MS, m/z 593 M$^{30}$ ·; NMR (CDCl$_3$) δ1.0 (t, CH$_2$CH$_2$DH$_3$), 1.72 (m, CH$_2$CH$_2$CH$_3$), 1.98 & 2.49 (2 m, H-3 & H-4), 3.44 (m, CH$_2$CH$_2$CH$_3$), 3.5 (t, CH$_2$CH$_2$S), 3.84, 3.86 & 3.89 (3 s, 3 OCH$_3$), 4.38 (t, SCH$_2$CH$_2$O), 5.22 (m, H-2 & H-5), 6.62 (s, C$_5$ArH), 7.28 & 7.48 (2 d, J=1.5 Hz, C$_2$ArH), 8.08 (s, triazole).

EXAMPLE 39 trans-2-[3-n-Propylsulfonyl-4-{2-(phenylthio) ethoxy-5-methoxyphenyl]-5-(3,4,5-trimethoxyphenyl) tetrahydrofuran This compound was prepared similarly as described before: MS, m/z 602 M$^{30}$ ·; NMR (CDCl$_3$): δ0.98 (t, CH$_2$CH$_2$CH$_3$), 1.72 (m, CH$_2$CH$_2$CH$_3$), 1.98 & 2.49 (2 m, H-3 & H-4), 3.4 (m, CH$_2$CH$_2$CH$_3$), 3.42 (t, CH$_2$CH$_2$S), 3.82 3.86 & 3.88 (3 s, 3 OCH$_3$), 4.32 (t, SCH$_2$CH$_2$O), 5.22 (m, H-2 & H-5), 6.60 (s, C$_5$ArH), 7.2-7.49 (m, ArH).

EXAMPLE 40 trans-2-[3-n-Propylsulfonyl-4-{2-phenylsulfinyl) ethoxy}-5-methoxyphenyl]-5-(3,4,5-trimethoxyphenyl) tetrahydrofuran m-Chloroperbenzoic acid (50 mg, 1.1 eq) was added to a solution of trans-2-[3-propylsulfonyl-4-{2-(phenylthio)ethoxy}-5-methoxyphenyl]-5-(3,4,5-trimethoxyphenyl) tetrahydrofuran (300 mg) in dichloromethane (3 mL), and the mixture was stirred at room temperature for 1 h. The solid was filtered off and the filtrate was washed with 1N NaOH, dried, and concentrated to a residue. Purification by flash column chromatography (hexane-ethyl acetate 1:2) afforded the title compound.

EXAMPLE 41 trans-2-[3-n-Propylsulfonyl-4-{2-(Phenylsulfonyl) ethoxy}-5-methoxyphenyl]-5-(3,4,5-trimethoxyphenyl( tetrahydrofuran m-Chloroperbenzoic acid (100 mg, 2.2 eq) was added to a solution of trans-2-[3-n-propylsulfonyl-4-Δ2-(phenylthio)ethoxy}-5-methoxyphenyl]-5-(3,4,5-trimethoxyphenyl) tetrahydrofuran (300 mg) in dichloromethane (3 mL), and the mixture was stirred at room temperature for 1 h. The solid was filtered off and the filtrate was washed with 1N NaOH, dried, and concentrated to a residue. Purification by flash column chromatography (hexane-ethyl acetate 1:1) afforded the title compound as a crystalline mass. Recrystallization from ethyl ether-hexane afforded pure product: MS, m/z 634 M$^{30}$·; NMR (CDCl$_3$): δ0.94 (t, CH$_2$CH$_2$CH$_3$), 1.63 (m, CH$_2$CH$_2$CH$_3$), 196 & 2.47 (2 m, H-3 & H-4), 3.4 (m, CH$_2$CH$_2$CH$_3$), 3.16 (t, CH$_2$CH$_2$SO$_2$), 3.82, 3.86 & 4.0 (3 s, 3 OCH$_3$), 4.49 (t, SO$_2$CH$_2$CH$_2$O), 5.20 (m, H-2 & H-5), 5.95 (s, C$_6$ArH), 7.24 & 7.43 (2 d, ArH), 7.6 (m, ArH) 8.0 (d, HArSO$_2$).

EXAMPLE 42 trans-2-[3-(2-N-Pyrrolidinylethylsulfonyl)-4,5-dipropoxyphenyl]-5-(3,4,5-trimethoxyphenyl) tetrahydrofuran

STEP 42A

1-[3-(2-Hydroxyethylthio)-4-hydroxy-5-benzyloxyphenyl]-4-(3,4,5-trimethoxyphenyl)butan-1,4-dione A mixture of 1-[3-bromo-4-hydroxy-5-benzyloxyphenyl]-4-(3,4,5-trimethoxyphenyl)butan-1,4-dione (30 g, 56.7 mmol), 2-hydroxyethyl disulfide (30 mL, 244 mmol) and copper powder (30 g) in dry pyridine (200 mL) was heated with vigorous stirring under reflux and nitrogen overnight. The progress of the reaction was monitored by TLC (hexane-ethyl acetate; 1:1, v/v). After the reaction was complete, the mixture was filtered hot over celite and washed with dichloromethane. The filtrates were combined and evaporated to a residue, which was partitioned between dichloromethane and 2N HCl. The organic layer was washed with water, dried, and concentrated to a small volume and passed through a sintered funnel of silica gel (100 g). The product was eluted with dichloromethane and then hexane-ethyl acetate (1:1, v/v). Fractions containing the desired product were combined and evaporated to dryness, and the residue was dissolved in a small volume of dichloromethane. Ethyl ether was added and crystals were collected and dried: R$_f$0.23 (hexane-ethyl acetate; 1:2, v/v); NMR (CDCl$_3$) δ 3.07 (t, J=6.0 Hz, SCH$_2$), 3.41 (COCH$_2$CH$_2$CO), 3.71 (t, SCH$_2$CH$_2$), 3.93 (s, 3 OCH$_3$), 5.18 (s, OCH$_2$C$_6$H$_5$), 7.30 (s, 2 H, C$_4$ArH), 7.37-7.45 (OCH$_2$e,uns/C/ $_6$H$_5$), 7.61 δ7.87 (2 d, J=1.5 Hz, 2 H, C$_1$ArH). The mother liquor, which contained some product as indicated by TLC, was not pursued further.

STEP 42B

1-[3-(2-Hydroxyethylsulfonyl)-4-hydroxy-5-benzyloxyphenyl]-4-(3,4,5-trimethoxyphenyl)butan-1,4-dione 3-Chloroper- benzoic acid (80-85%; 8.5 g, 39.4 mmol) was added to a solution of 1-[3-(2-hydroxyethylthio)-4-hydroxy-5-benzyloxyphenyl -4-(3,4,5-trimethoxyphenyl) butan-1,4-dione (9.4 g, 17.9 mmol) in dichloromethane (80 mL). The mixture was stirred at room temperature for 6 h, filtered, and the filtrate was concentrated to a small volume. Ethyl ether was added and crystals were collected and washed with Et$_2$O: mp 129°-130° C; R$_f$0.26 (chloroform-methanol; 9:1, v/v): NMR (CDCl$_3$) δ3.44 (COCH$_2$CH$_2$CO), 3.64 (t, SOCH$_2$), 4.08 (t, SOCH$_2$CH$_2$), 3.94 (s, 3 OCH$_3$), 5.22 (s, OCH$_2$C$_6$H$_5$), 7.30 (s, 2 H, C$_4$ArH), 7.43 (OCH$_2$C$_6$H$_5$), 7.87 & 8.20 (2 d, J=1.5 Hz, 2 H, C$_1$ArH).

STEP 42C

1-[3-(2-Hydroxyethylsulfonyl)-4-n-propoxy-5-benzyloxyphenyl]-4-(3,4,5-trimethoxyphenyl)butan-1,4-dione n-Propyl bromide (1.63 mL, 17.8 mmol) was added to a solution of 1-[3-(2-hydroxyethylsulfonyl)-4-hydroxy-5-benzyloxyphenyl]-4-(3,4,5-trimethoxyphenyl)butan-1,4-dione (5.53 g, 9.91 mmol) in DMF (10 mL) containing postassium carbonate (2.74 g, 19.9 mmol). The mixture was stirred at 75° C. for 2 h, and partitioned between ethyl ether and water. The aqueous layer was re-extracted with ether (2 ×) and ethyl acetate. The organic extracts were combined, dried, and evaporated to dryness. The residue was triturated with Et₂O to give crystals, which was washed with Et₂O containing a small volume of acetone. This material, R_f 0.53 (hexane-ethyl acetate; 1:2, v/v), was used directly in the next experiment without further purification.

STEP 42D

1-[3-(2-Hydroxyethylsulfonyl)-4-n-propoxy-5-benzyloxyphenyl]-4-(3,4,5-trimethoxyphenyl)butan-1,4-dione Sodium borohydride (0.66 g) was added to a suspension of 1-[3-(2-hydroxyethylsulfonyl)-4-propoxy-5-benzyloxyphenyl]-4-(3,4,5-trimethoxyphenyl)butan-1,4-dione (from previous experiment) with ethanol (125 mL), and the mixture was heated at 75° C. for 2 h. The solution was cooled and diluted with dichloromethane. It was then washed with 2.5 N HCl (2 ×) and water, dried, and evaporated to a syrup, R_f 0.11 (hexane-ethyl acetate; 1:1, v/v). This material was used directly in the next experiment without further purification.

STEP 42E trans-2-[3-(2-Hydroxyethylsulfonyl)-4-n-propoxy-5-benzyloxyphenyl]-5-(3,4,5-trimethoxyphenyl)tetrahydrofuran A solution of 1-[3-(2-hydroxyethylsulfonyl)-4-propoxy-5-benzyloxyphenyl]-4-(3,4,5-trimethoxyphenyl)butan-1,4-diol (from previous experiment) in chloroform (20 mL) was treated with 10% trifluroacetic acid (20 mL). The reaction was monitored by TLC. After 1 h, anhydrous sodium carbonate was added, and the solid was filtered off and washed with chloroform. The solvent was evaporated and the residue was passed through a flash column of silica gel (hexane-ethyl acetate; 2:1, v/v). The cis- and trans-isomers were then separated by HPLC (hexane-ethyl acetate; 1:1, v/v): mp 112°–113° C.; R_f 0.33 (hexane-ethyl acetate; 1:1, v/v): NMR (CDCl₃) δ0.98 (t, J=7.5 Hz, CH₂CH₂CH₃), 1.83 (m, CH₂CH₂CH₃), 2.85 (t, J=6.5 Hz, OH), 3.67 (q, SO₂CH₂), 3.98 (q, SO₂CH₂CH₂), 4.17 (t, CH₂CH₂CH₃), 5.18 (s, CH₂C₆H₅), 6.63 (s, 2 e,uns/H/, C₅ArH).

STEP 42F trans-2-[3-(2-Hydroxyethylsulfonyl)-4-n-propoxy-5-hydroxyphenyl]-5-(3,4,5-trimethoxyphenyl)tetrahydrofuran A solution of trans-2-[3-(2-hydroxyethylsulfonyl)-4-n-propoxy-5-benzyloxyphenyl]05-(3,4,5-trimethoxyphenyl)tetrahydrofuran (440 mg) in ethyl acetate (6 mL) was hydrogenated over 10% palladium-on-charcoal (120 mg) at 45 psi for 1 h. The catalyst was filtered off and washed with ethyl acetate. The combined filtrates were evaporated to give the title compound: R_f 0.1 (hexane-ethyl acetate; 1:1 v/v); NMR (CDCl₃) δ107 (t, CH₂CH₂CH₃), 3.60 (q, SO₂CH₂), 3.95 (q, SO₂CH₂CH₂), 3.84 (s, OCH₃), 3.88 (s, 2 OCH₃), 4.11 (t, CH₂CH₂CH₃), 5.13–5.25 (m, H- 2 & H-5), 6.61 (s, 2 H, C₅ArH), 7.32 & 7.49 (2 d, J=2.0 Hz, C₂ArH).

STEP 42G trans-2-[3-(2-Hydroxyethylsulfonyl)-4,5-di-n-propoxyphenyl]-5-(3,4,5-trimethoxyphenyl)tetrahydrofuran A mixture of trans-2-[3-(2-hydroxyethylsulfonyl)-4-n-propoxy-5-hydroxyphenyl]-5-(3,4,5-trimethoxyphenyl)tetrahydrofuran (366 mg, 0.74 mmol), n-propyl bromide (0.12 mL, 1.33 mmol) and potassium carbonate (255 mg, 1.85 mmol) in DMF (3 mL) was heated at 75° C. for 1 h. The reaction mixture was cooled and partitioned between ethyl ether and water, and the aqueous layer was re-extracted with ether (2 ×). The organic extracts were combined, dried, and evaporated to dryness. The residue was purified by chromatography to give the title compound: R_f 0.43 (hexane-ethyl acetate; 1:2, v/v); NMR (CDCl₃) δ1.05 & 1.09 (2 t, J=7.5 Hz, 2 CH₂CH₂CH₃), 2.85 (t, J=6.5 Hz, OH), 3.65 (m, SO₂CH₂), 3.95 (m, SO₂CH₂CH₂), 4.03 & 4.15 (2 t, J=6.5 Hz, 2 CH₂CH₂CH₃), 6.63 (s, 2 H, C₅ArH), 7.27 & 7.49 (2 d, J=1.5 Hz, C₂ArH).

STEP 42H trans-2-]3-(2-(-Methanesulfonylethylsulfonyl)-4,5-di-n-propoxyphenyl]-5-(3,4,5-trimethoxyphenyl)tetrahydrofuran Methanesulfonyl chloride (0.097 mL, 1.25 mmol) was added to a solution of trans-2-[3-(2-hydroxyethylsulfonyl)-4,5-di-n-propoxyphenyl]-5-(3,4,5-trimethoxyphenyl)tetrahydrofuran (338 mg, 0.63 mmol) in dichloromethane (3 mL) and pyridine (1.3 mL). The reaction mixture was stirred at room temperature for 2 h, and worked-up as usual to give a syrup, R_f 0.52 (hexane-ethyl acetate; 1:2 v/v). This material was used directly in the next experiment without further purification.

STEP 42I trans-2-(3-Vinylsulfonyl-4,5-di-n-propoxyphenyl)-5-(3,4,5-trimethoxyphenyl)tetrahydrofuran A solution of trans-2-[3-(2-)-methanesulfonylethylsulfonyl)-4,5-di-n-propoxyphenyl]-5-(3,4,5-trimethoxyphenyl) tetrahydrofuran (387 mg, from previous experiment) in dichloromethane (5 mL) was treated with triethylamine (0.24 mL) for 30 min at room temperature. The solution was evaporated to a residue, which was purified by flash column chromatography (hexane-ethyl acetate; 3:1, v/v): R_f 0.38 (hexane-ethyl acetate: 1:1, v/v); NMR (CDCl₃)δ1.06 & 1.09 (2 t, J=7.5 Hz, 2 CH₂CH₂CH₃), 4.01 & 4.15 (2 t, J=6.5 Hz, J=7.0 Hz, 2 CH₂CH₂CH₃), 5.16–5.27 (m, H-2 & H-5), 6.03 & 6.46 (2 d, J=10.0 Hz, J=17.0 Hz, SO₂CH=CH₂), 6.64 (s, 2 H, C₅ArH), 7.04 (2 d, SO₂H=CH₂), 7.24 & 7.51 (2 d, J=1.5 Hz, C₂ArH).

STEP 42J trans-2-[3-(2-N-pyrrolidinylethylsulfonyl)-4,5-di-n-propoxyphenyl]-5-(3,4,5-trimethoxyphenyl)tetrahydrofuran A solution of trans-2-(3-vinylsulfonyl-4,5-di-n-propoxyphenyl)-5-(3,4,5-trimethoxyphenyl)tetrahydrofuran (30 mg, 0.06 mmol) and pyrrolidine (0.03 mL) in acetonitrile (3 mL) was kept at room temperature for 6 h and evaporated to dryness. Purification by preparative TLC (CHCl₃-MeOH; 95.5, v/v) gave the title compound: R_f 0.29; MS, m/z 592 (M+1)⁺; NMR (CDCl₃) δ1.05 & 1.09 (2 t, J=7.5 Hz, 2 CH₂CH₂CH₃), 1.72 & 2.49 ]2 b, N(CH₂)₄], 2.86 (q, SO₂CH₂CH₂), 3.65 (q, SO₂CH₂CH₂), 3.86 (s, OCH₃), 3.89 (s, 2 OCH₃),4.02 & 4.14 (2 t, J=6.0 Hz, J=6.5 Hz, 2 CH₂CH₂CH₃), 5.16–5.28 (m, H-2 & H-5), 6.64 (s, 2 H, C₅ArH), 7.25 & 7.46 (2 d, J=1.5 Hz, 2 H, C₂ArH).

EXAMPLE 43 trans-2-[3-(2-N-Morpholinoethylsulfonyl)-4,5-di-n-propoxyphenyl]-5-(3,4,5-trimethoxyphenyl)tetrahydrofuran A solution of trans-2-(3-vinylsulfonyl-4,5-di-n-propoxyphenyl)-5-(3,4,5-trimethoxyphenyl) tetrahydrofuran (30 mg, 0.06 mmol) and morpholine (0.02 mL) in acetonitrile (3 mL) was kept at room temperature for 4 h and evaporated to dryness. Purification by preparative TLC ($CHCl_3$-MeOH; 95.5; v/v) gave the title compound: MS, m/z 607 (M+1)$^+$; NMR ($CDCl_3$) $\delta$1.05 & 1.09 (2 t, J=7.5 Hz, 2 $CH_2CH_2CH_3$), 2.37 & 3.50 ]2 b, $N(CH_2)_2O(CH_2)_2$]2.77 (m, $SO_2CH_2CH_2$), 3.63 (m, $CO_2CH_2CH_2$), 4.02 & 4.14 (2 t, J=6.5 Hz, 2 $CH_2CH_2CH_3$), 5.16-5.28 (m, H-2 & H-5), 6.63 (s, 2 H, $C_5ArH$), 7.25 & 7.46 (2 d, 2 H, $C_2ArH$).

EXAMPLE 44 trans-2-[3-n-Propylsulfonyl-4-(6-hydroxy-n-hexyloxy)-5-{2-(1-morpholino)-ethoxy}phenyl]5-(3,4,5-trimethoxyphenyl)tetrahydrofuran

STEP 44A trans-2-[3-n-Propylsulfonyl-4-(carboethoxy-n-pentyloxy)-5-hydroxyphenyl]-5-trimethoxyphenyl)tetrahydrofuran This compound was prepared from the appropriate starting materials according to procedures as outlined in Example 1, Step L. MS, m/z 594 M$^+$; NMR (CDCl3, 200 MHz) $\delta$1.0 (t, $CH_2CH_2CH_3$), 1.28 (t, $-CO_2CH_2CH_3$), 1.6-1.8(m, $O-CH_2CH_2HCH_2CH_2CH_2CO_2Et$), 1.9(m, $CH_2CH_2CH_3$), 2.0,2.45(2M, H-3,H-4), 2.4(t, $CH_2CO_2Et$), 3.3(m, $SO_2CH_2CH_2CH_3$), 3.86, 3.92(2s, 3 $OCH_3$), 4.16(q, $-OCH_2(CH_2)_4-CO_2CH_2CH_3$), 5.22(m, H-2,H-5), 6.62(s, $C_5ArH$), 7.3,7.5(2d, J=1.5Hz,$C_2ArH$).

STEP 44B trans-2-[3-n-Propylsulfonyl-4-(carboethoxy-n-pentyloxy)-5-{2-(1-morpholino)}phenyl]-5-trimethoxyphenyl)tetrahydrofuran This compound was prepared from the appropriate starting materials according to procedures as outlined in Example 1, Step N. MS, m/z 707 M$^+$; NMR (CDCl3, 200MHz) $\delta$1.0 (t, $CH_2CH_2CH_3$), 1.28 (t, $-CO_2CH_2CH_3$), 1.6-2.06 (m, $O-CH_2CH_2CH_2CH_2CH_2CO_2Et$, $CH_2CH_2CH_3$, H-4), 2.36 (t, $CH_2CO_2Et$), 2.5(3m, $-CH_2N(CH_2-CH_2)_2O$, H-3), 3.36(m, $SO_2CH_2CH_2CH_3$), 3.72(m, $-CH_2N(CH_2-CH_2)_2O$), 3.86, 3.92(2s, 3 $OCH_3$), 4.08-4.22(3-m,$-OCH_2(CH_2)_4-CO_2CH_2CH_3$, $OCH_2CH_2N$), 5.22(m, H-2, H-5), 6.62(s, $C_5ArH$), 7.3,7.5(2d, J=1.5Hz, $C_2ArH$).

STEP 44C trans-2-[3-n-Propylsulfonyl-4-(6-hydroxyhexyloxy)-5-{2-(1-morpholino)ethoxy}phenyl]-5-trimethoxyphenyl)tetrahydrofuran The title compound was prepared from trans-2-[3-n-Propylsulfonyl-4-(carboethoxy-n-pentyloxy)-5-{2-(1-morpholino) ethoxy}phenyl]-5-trimethoxyphenyl)tetrahydrofuran with $LiAlH_4$ in THF at 0° C. after purification by chromatography on silica gel eluting with ethyl acetate. MS, m/z 665 M$^{30}$. NMR (CDCl3, 200 MHz) $\delta$1.0 (t, $CH_2CH_2CH_3$), 1.4-2.04 (m, $-O-CH_2-(CH_2)_4$ $-CH_2-OH$, $SO_2CH_2CH_2CH_3$, 2.86(m, $-CH_2N(CH_2-CH_2)_2O$), 3.38(m, $SO_2CH_2CH_2CH_3$), 3.6-3.8(m, $-O-CH_2(CH_2)_4-CH_2-OH,-CH_2N(CH_2-CH_2)_2O$), 3.86, 3.92(2s, 3 $OCH_3$), 4.08-4.2(m, $-O-CH_2(CH_2)_4-CH_2-OH$, $OCH_2CH_2N$), 5.22(m, H-2,H-5), 6.62(s, $C_5ArH$), 7.3,7.5(2d, J=1.5Hz,$C_2ArH$).

EXAMPLE 45 trans-2-]3-n-Propylsulfonyl-4-(6-hydroxyhexyloxy)-5-{3-(1-morpholino)n-propoxy}phenyl]-5-trimethoxyphenyl)tetrahydrofuran This compound was prepared from the appropriate starting materials according to procedures as outlined in Example 44: MS, m/z 679 M$^+$; NMR (CDCl3, 200 MHz) $\delta$1.0 (t, $CH_2CH_2CH_3$), 1.4-2.0(m, $-O-CH_2(CH_2)_4$ $CH_2OH$, $SO_2CH_2CH_2CH_3$, $OCH_2CH_2CH_2N$, H-4), 2.5(m, $-CH_2N(CH_2-CH_2)_2O$, H-3), 3.38(m, $SO_2CH_2CH_2CH_3$), 3.6-3.8(m, $-O-CH_2(CH_2)_4-CH_2-OH,-CH_2N(CH_2-CH_2)_2O$), 3.86,3.92(2s, 3 $OCH_3$), 4.06-4.2(m,$-O-CH_2-(CH_2)_4CH_2-OH,OCH_2CH_2N$),5.22(m, H-2,H-5), 6.62(s, $C_5ArH$), 7.3,7.5(2d, J=1.5Hz, $C_2ArH$).

EXAMPLE 46 trans-2-[3-(3-Hydroxybutyl)sulfonyl-4-n-propoxy-5-(3-{1-morpholino}-n-propoxy)phenyl]-5-(3,4,5-trimethoxyphenyl)tetrahydrofuran

STEP 46A trans-2-[3-(3-Hydroxypropylsulfonyl)-4-n-propoxy-5-benzyloxyphenyl]-5-(3,4,5-trimethoxyphenyl)tetrahydrofuran 834 mg of trans-2-[3-methylsulfonyl-4-n-propoxy-5-benzyloxyphenyl]-5-(3,4,5-trimethoxyphenyl)tetrahydrofuran dissolved in 8 ml of dry THF was cooled to $-78°$ C. and to it was added 2 ml of n-butyllithium (1.6 N solution in THF) in nitrogen atmosphere. After 15 min. 140 mg of bromoethanol dissolved in 2 ml of THF was added to the reaction mixture. The yellow solution was warmed to room temperature and was quenched with a saturated $NH_4Cl$ solution. The title compound was obtained after workup and chromatography on silica gel: MS, m/z 600 M$^+$; NMR (CDCl3, 200MHz) $\delta$1.0(t, $OCH_2CH_2CH_3$), 1.82 (q,$OCH_2CH_2CH_3$), 1.0-2.4(m, $SO_2CH_2CH_2CH_2OH$, H-4), 2.5(m,H-3), 3.58 (t,$SO_2CH_2CH_2CH_2OH$), 3.72(m, $CH_2OH$), 3.86, 3.92(2s,3 $OCH_3$), 4.18 (t,$OCH_2CH_2CH_3$), 5.18(s, $OCH_2Ar$), 5.08-5.22 (m,H-2,H-5), 6.62(s,$C_5ArH$), 7.28-7.54(-m,ArH).

STEP 46B trans-2-[3-(3-Oxopropyl)sulfonyl-4-n-propoxy-5-benzyloxyphenyl]-5-(3,4,5-trimethoxyphenyl)tetrahydrofuran To a solution of 600 mg of trans-2-[3-(3-hydroxypropylsulfonyl-4-n-propoxy-5-benzyloxyphenyl]-5-(3,4,5-trimethoxyphenyl) tetrahydrofuran in methylene chloride at room temperature was added 650 mg of pyridinium chlorochromate. After 4 hours at room temperature the reaction was washed with water, dilute HCl, brine, dried over $MgSO_4$ and evaporated to provide the title compound which was used without further purification.

STEP 46C trans-2-[3-(3-hydroxybutyl)sulfonyl-4-n-propoxy-5-benzyloxyphenyl]-5-(3,4,5-trimethoxyphenyl)tetrahydrofuran To a solution of 400 mg of trans-2-[3-(3-oxopropylsulfonyl-4-n-propoxy-5-benzyloxyphenyl]-5-(3,4,5-trimethoxyphenyl) tetrahydrofuran in 5 ml of THF at 0° C. was added 0.5 ml of methylmagnesiumbromide (3.0 M solution in ether). The reaction stirred for 1 hour whereupon it was allowed to warm to room temperature and quenched with a saturated solution of $NH_4Cl$ and worked up as usual and purified by chromatography on silica gel eluting with ethylacetate: hexanes, 2:3 to provide the title compound: MS, m/z 614 $M^{30}$; NMR ($CDCl_3$, 200MHz) δ1.0(t, $OCH_2CH_2CH_3$), 1.22(d, $CH_2CH(OH)CH_3$) 1.66-2.04 (m, $O\overline{CH_2}CH_2CH_3$, $SO_2CH_2\overline{CH_2}CH(OH)CH_3$, H-4), 2.5(m,H-3), 3.58(t,$SO_2\overline{CH_2}CH_2CH(OHCH_3)$), 3.86, 3.92(2s,3 $OCH_3$), 4.$\overline{18}$(t,$OCH_2CH_2CH_3$), 5.18(s, $OCH_2Ar$), 5.08-5.24(m,H-2,H-$\overline{5}$), 6.62(s,$C_5ArH$), 7.28-$\overline{7}$.567(-m,ArH).

STEP 46D trans-2-[3-(3-Hydroxybutyl)sulfonyl-4-n-propoxy-5-(3-{1-morpholino}-n-propoxy)phenyl]-5-(3,4,5-trimethoxyphenyl)tetrahydrofuran The title compound was prepared according to procedures described in Example 1, Step N. MS, m/z 651 M+; NMR (CDCl3, 200MHz) δ1.0 (t, $OCH_2CH_2CH_3$), 1.22 (d, $CH_2CH(OH)CH_3$) 1.70-2.16 (m, $O\overline{CH_2}CH_2CH_3$, $SO_2CH_2\overline{CH_2}CH(OH)CH_3$, H-4), 2.4-2.62 (m,H-3, $CH_2N(CH_2CH_2)_2O$), 3.56 (t, $SO_2\overline{CH_2}CH_2CH(OH)CH_3$), 3.74 (m, $CH_2\overline{N}(CH_2CH_2)_2O$), 3.86, 3.92 (2s, 3 $OCH_3$), 4.08-4.18 (t, $OCH_2CH_2CH_3$, $OCH_2CH_2CH_2N$), 5.22 (m, H-2,H-5), 6.62 (s,$C_5ArH$), 7.28-7.5 (m,ArH).

EXAMPLE 47 trans-2-[3-(2-hydroxypropyl)sulfonyl-4-n-propoxy-5-(2-imidazolyl)methoxyphenyl]-5-(3,4,5-trimethoxyphenyl)tetrahydrofuran The title compound was prepared in a manner analogous to the procedures described in Examples 1 and 2, except that the alkylation is done with 1-benzyl-2-chloro- methylimidazole and the benzyl group was subsequently removed by catalytic hydrogenation. NMR (CDCl3, 200MHz) δ1.0(t, $OCH_2CH_2CH_3$), 1.36(d,$CH_2CH(OH)CH_3$) 1.65-2.16(m,$OCH_2\overline{CH_2}CH_3$, H-4), 2.46(m,H-3), 3.5(m,$SO_2\overline{CH_2}CH(OH)CH_3$), 3.85, 3.89(2s,3 OCH3), 4.1(m,$\overline{O}CH_2CH_2CH_3$),4.3(m, $CH(OH)CH_3$) 5.1-5.4(m,H-$\overline{2}$,H-5,—$CH_2$—Im), 6.$\overline{62}$(s,$C_5ArH$), 7.1-7.59(m,ArH,imidazole protons).

What is claimed is:

1. A compound of the following structural formula:

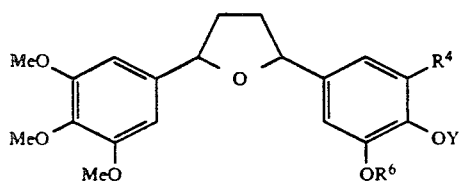

wherein:
R⁴ is [(a)]S(O)$_n$ R², in which n is 0, 1 or 2, and
R² is selected from the group consisting of
  (1) $C_{1-6}$alkyl,
  (2) substituted $C_{1-6}$alkyl wherein the substituent is selected from the group consisting of hydroxy, and amino,
  (3) $C_{2-6}$alkenyl,
  (4) $C_{1-6}$alkylcarbonyl-$C_{1-6}$alkyl,
  (5) N-substituted $C_{10-6}$aminoalkyl, wherein the substituent is $C_{1-6}$alkyl,
  (6) N,N-di-substituted $C_{1-6}$aminoalkyl, wherein the substituents each independently represent $C_{1-6}$alkyl,
  (7) imidazolyl-$C_{1-6}$alkyl;
Y is selected from the group consisting of
  (a) $C_{1-12}$alkyl,
  (b) substituted $C_{1-8}$alkyl wherein the substituent is selected from the group consisting of hydroxy, and amino,
  (c) $C_{1-8}$alkoxy-$C_{1-6}$alkyl,
  (d) $C_{2-6}$alkenyl,
  (e) $C_{1-6}$alkyl S(O)$_m$-$C_{1-6}$alkyl in which m is 0, 1 or 2, and
  (f) imidazolylthio-$C_{1-6}$alkyl;
R⁶ is selected from the group consisting of
  (a) $C_{1-6}$alkyl,
  (b) substituted $C_{1-6}$alkyl wherein the substituent is selected from the group consisting of hydroxy and amino,
  (c) $C_{1-6}$alkyl—O—$R^{10}$, wherein $R^{10}$ is
    (1) —$PO_2(OH)^-$ M⁺ wherein M⁺ is a pharmaceutically acceptable cation,
    (2) —C(O)(CH₂)₂—$CO_2^-$ M⁺, or
    (3) —$SO_3^-$M⁺,
  (d) $C_{1-6}$-alklcarbonyl-$C_{1-6}$alkyl,
  (e) $C_{1-6}$carboxyalkyl,
  (f) $C_{1-4}$alkylamino-$C_{1-6}$alkyl,
  (g) N,N-di-substituted $C_{1-6}$aminoalkyl wherein the substituents each independently represent $C_{1-6}$alkyl,
  (h) imidazolyl-$C_{1-6}$alkyl, and
  (i) imidazolyl-X—$C_{1-6}$alkyl wherein X is thio or amino;
provided that at least one of R⁴, Y and R⁶ contains an imidazolyl.

2. A compound of claim 1 wherein the substituents at positions 2 and 5 of the tetrahydrofuran are in a trans relationship to one another.

3. A compound according to claim 2 wherein R⁴ is S(O)$_n$ R², n is 2 and R² is selected from the group consisting of
  (a) $C_{1-6}$alkyl,
  (b) substituted $C_{1-6}$alkyl wherein the substituent is selected from the group consisting of hydroxy, oxo and amino,
  (c) N-substituted $C_{1-6}$aminoalkyl, wherein the substituent is $C_{1-6}$alkyl, and
  (d) N,N-di-substituted $C_{1-6}$aminoalkyl, wherein the substituents each independently represent $C_{1-6}$alkyl; and
R⁶ is selected from the group consisting of
  (a) imidazolyl-$C_{1-6}$alkyl, and
  (b) imidazolyl-X-$C_{1-6}$alkyl wherein X is thio or amino.

4. A compound according to claim 3 wherein Y is $C_{1-12}$alkyl or hydroxy $C_{1-8}$alkyl.

5. A compound according to claim 4 wherein R² is selected from the group consisting of
  (a) $C_{1-3}$alkyl, (b) $C_{1-3}$alkylcarbonyl-$C_{1-3}$alkyl, and
(c) hydroxy $C_{1-4}$alkyl; and
Y is n-propyl.

6. A compound of claim 5 which is:
(a) trans-2-[3-(2-Oxopropylsulfonyl)-4-propoxy-5-{3-(1-imidazolyl)propoxy}phenyl]-5-(3,4,5)-trimethoxyphenyl) tetrahydrofuran,
(b) trans-2-[3-(2-Hydroxypropylsulfonyl)-4-n-propoxy-5-{2-(1-imidazolyl)ethoxy}phenyl]-5-(3,4,5-trimethoxyphenyl) tetrahydrofuran,
(c) trans-2-[3-(2-Hydroxypropylsulfonyl)-4-n-propoxy-5-{3-(1-imidazolyl)propoxy}phenyl]-5-(3,4,5-trimethoxyphenyl) tetrahydrofuran,
(d) trans-2-[3-(2-Hydroxypropylsulfonyl)-4-n-propoxy-5-{4-(1-imidazolyl)butoxy}phenyl]-5-(3,4,5-trimethoxyphenyl) tetrahydrofuran,
(e) trans-2-[3-(2-Hydroxypropylsulfonyl)-4-n-propoxy-5-{2-(2-imidazolylthio) ethoxy}phenyl]-5-(3,4,5-trimethoxyphenyl)tetrahydrofuran,
(f) trans-2-[3-(2-Hydroxypropylsulfonyl)-4-n-propoxy-5-{3-(2-imidazolylthio) propoxy}phenyl]-5-(3,4,5-trimethoxyphenyl)tetrahydrofuran,
(g) trans-2-[3-(2-Oxopropylsulfonyl)-4-n-propoxy-5-{2-(2-imidazolylthio) ethoxy}phenyl]-5-(3,4,5-trimethoxyphenyl)tetrahydrofuran,
(h) trans-2-[3-(2-Oxopropylsulfonyl)-4-n-propoxy-5-{3-(2-imidazolylthio) propoxy}phenyl]-5-(3,4,5-trimethoxyphenyl)tetrahydrofuran,
(i) trans-2-[3-(2-Oxopropylsulfonyl)-4-n-propoxy-5-{4-(2-imidazolylthio) butoxy}phenyl]-5-(3,4,5-trimethoxyphenyl)tetrahydrofuran, or
(j) trans-2-[3-(2-hydroxypropyl)sulfonyl-4-n-propoxy-5-(2-imidazolyl)sulfonyl-4-n-propoxy-5-(2-imidazolyl)-methoxyphenyl]-5-(3,4,5-trimethoxyphenyl) tetrahydrofuran,
or a stereochemical isomer thereof in the (2S,5S) configuration.

7. A compound of claim 6 which is trans-2-[3-(2-Oxopropylsulfonyl)-4-propoxy-5-{3-(1-imidazolyl)propoxy}phenyl]-5-(3,4,5)-trimethoxyphenyl) tetrahydrofuran.

8. A compound of claim 7 in the (−)-(2S,5S) configuration which is
(−)-(2S,5S)-2-[3-(2-Oxopropylsulfonyl)-4-propoxy-5-{3-(1-imidazolyl)propoxy} phenyl]-5-(3,4,5)-trimethoxyphenyl) tetrahydrofuran.

9. A compound according to claim 2, wherein
$R^4$ is (a) $S(O)_n$ $R^2$, in which n is 2, and
$R^2$ is imidazolyl$C_{1-6}$alkyl.

10. A compound according to claim 9 wherein
$R_6$ is selected from the group consisting of
(a) $C_{1-6}$alkyl,
(b) substituted $C_{1-6}$alkyl wherein the substituents is selected from the group consisting of hydroxy and amino,
(c) $C_{1-6}$alkylcarbonyl-$C_{1-6}$alkyl,
(d) $C_{1-6}$carboxyalkyl, and
(e) N,N-di-substituted $C_{1-6}$aminoalkyl wherein the substituent is $C_{1-6}$alkyl.

11. A compound according to claim 2 wherein
Y is imidazolylthio-$C_{1-6}$alkyl.

12. A compound according to claim 11 wherein
$R^4$ is $S(O)_n$ $R^2$, n is 2 and $R^2$ is selected from the group consisting of
(a) $C_{1-6}$alkyl,
(b) substituted $C_{1-6}$alkyl wherein thge substituent is selected from ther group consisting of hydroxy and amino,
(c) $C_{2-6}$alkenyl,
(d) $C_{1-6}$alkylcarbonyl-$C_{1-6}$alkyl, and
(e) $C_{1-6}$diaminoalkyl.

13. A compound according to claim 12 wherein
$R_6$ is selected from the group consisting of
(a) $C_{1-6}$alkyl,
(b) substituted $C_{1-6}$alkyl wherein the substituent is selected from the group consisting of hydroxy and amino,
(c) $C_{1-6}$alkylcarbonyl-$C_{1-6}$alkyl,
(d) $C_{1-6}$carboxyalkyl, and
(e) N,N-disubstituted amino-$C_{1-6}$-alkyl wherein the substituents each independently represent $C_{1-6}$alkyl.

14. A compound according to claim 13 which is trans-2-[3-n-Propylsulfonyl-4-{2-(2-imidazolthio)ethoxy}-5-methoxyphenyl]-5-(3,4,5-trimethoxyphenyl) tetrahydrofuran,
and a stereochemical isomer thereof in the (2S,5S) configuration.

15. A pharmaceutical composition for antagonizing the effects of PAF which comprises a nontoxic therapeutically effective amount of a compound according to claim 2 and a pharmaceutically acceptable carrier.

16. A method of antagonizing the effects of PAF in a subject in need thereof which comprises administering to said subject a nontoxic therapeutically effective amount of a compound according to claim 2.

* * * * *